United States Patent
Parsa et al.

(10) Patent No.: US 9,683,996 B2
(45) Date of Patent: Jun. 20, 2017

(54) ASSESSMENT OF SOLID TUMOR BURDEN

(75) Inventors: Andrew T. Parsa, San Francisco, CA (US); Lewis L. Lanier, San Francisco, CA (US); Courtney Crane, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 698 days.

(21) Appl. No.: 13/503,009

(22) PCT Filed: Oct. 22, 2010

(86) PCT No.: PCT/US2010/053855
§ 371 (c)(1),
(2), (4) Date: Aug. 8, 2012

(87) PCT Pub. No.: WO2011/050328
PCT Pub. Date: Apr. 28, 2011

(65) Prior Publication Data
US 2012/0322668 A1    Dec. 20, 2012

Related U.S. Application Data

(60) Provisional application No. 61/254,170, filed on Oct. 22, 2009.

(51) Int. Cl.
*G01N 33/574* (2006.01)

(52) U.S. Cl.
CPC . *G01N 33/57492* (2013.01); *G01N 33/57407* (2013.01); *G01N 33/57415* (2013.01); *G01N 33/57434* (2013.01); *G01N 33/57438* (2013.01); *G01N 2800/52* (2013.01)

(58) Field of Classification Search
None
See application file for complete search history.

(56) References Cited

U.S. PATENT DOCUMENTS

2005/0233391 A1    10/2005  Spies et al.
2006/0280755 A1    12/2006  Baron et al.
2009/0181394 A1     7/2009  Chung

OTHER PUBLICATIONS

International Search Report and Written Opinion received for PCT Patent Application No. PCT/US2010/53855, mailed on Jul. 7, 2011, 11 pages.
International Preliminary Report on Patentability received for PCT Patent Application No. PCT/US2010/053855, mailed on May 3, 2012, 7 pages.
Crane et al., (2010). "TGF-β Downregulates the Activating Receptor NKG2D on NK Cells and CD8 T Cells in Glioma Patients", Neuro-Oncology, 12:7-13.
Crane et al., (2014). "Immune Evasion Mediated by Tumor-Derived Lactate Dehydrogenase Induction of NKG2D Ligands on Myeloid Cells in Glioblastoma Patients", Proc. Natl. Acad. Sci. USA, 111,:12823-12828.
Eruslanov et al., (2009). "Altered Expression of 15-Hydroxyprostaglandin Dehydrogenase in Tumor-Infiltrated CD11b Myeloid Cells: A Mechanism for Immune Evasion in Cancer", J. Immunol. 182:7548-7557.
Friese et al., (2004). "RNA Interference Targeting Transforming Growth Factor-β Enhances NKG2D-Mediated Antiglioma Immune Response, Inhibits Glioma Cell Migration and Invasiveness, and Abrogates Tumorigenicity In Vivo", Cancer Research, 64:7596-7603.
Groh et al., (1996). "Cell Stress-Regulated Human Major Histocompatibility Complex Class I Gene Expressed in Gastrointestinal Epithelium", Proc. Natl. Acad. Sci. USA, 93:12445-12450.
Groh et al., (1999). "Broad Tumor-Associated Expression and Recognition by Tumor-Derived Gamma Delta T Cells of MICA and MICB", Proc. Natl. Acad. Sci. USA, 96:6879-6884.
Groh et al., (2002). "Tumour-Derived Soluble MIC Ligands Impair Expression of NKG2D and T-Cell Activation", Nature, 419:734-738.
Rebmann et al., (2007). "Soluble MICA as an Independent Prognostic Factor for the Overall Survival and Progression-Free Survival of Multiple Myeloma Patients", Clin. Immunol., 123:114-120.
Extended European Search Report (includes Supplementary European Search Report and Search Opinion) received for European Patent Application No. 10825788.2, mailed on Mar. 19, 2013, 6 pages.

*Primary Examiner* — Nancy Treptow
(74) *Attorney, Agent, or Firm* — Morrison & Foerster LLP

(57) ABSTRACT

The present disclosure is directed toward measurement of expression of one or both of an activating Natural Killer (NK) cell receptor and its ligand(s) on peripheral blood cells as a means to assess solid tumor burden. In particular, the present disclosure provides tools for assessing cancer recurrence or risk thereof following reduction of a solid tumor, and for developing a treatment regime for a cancer patient.

17 Claims, 19 Drawing Sheets

ASSESSMENT OF SOLID TUMOR BURDEN

CROSS-REFERENCE TO RELATED APPLICATIONS

This application is a U.S. National Phase patent application of PCT/US2010/053855, filed Oct. 22, 2010, which claims the benefit under 35 USC 119(e) of U.S. Provisional Patent Application No. 61/254,170, filed Oct. 22, 2009, each of which is incorporated herein by reference in its entirety for all purposes.

STATEMENT OF GOVERNMENT SUPPORT

This invention was made with United States Government support under the National Cancer Institute Specialized Program of Research Excellence grant 2 P50 CA097257-06, and under the National Institutes of Health grant AI066897. The United States Government has certain rights in the invention.

FIELD

The present disclosure is directed toward measurement of expression of one or both of an activating Natural Killer (NK) cell receptor and its ligand(s) on peripheral blood cells as a means to assess solid tumor burden. In particular, the present disclosure provides tools for assessing cancer recurrence or risk thereof following reduction of a solid tumor, and for developing a treatment regime for a cancer patient.

BACKGROUND

In patients with some types of tumors, the most reliable method for identifying a recurrence is radiologic imaging. For example patients with brain tumors are routinely followed using MRI scans with and without contrast. These modalities are often subject to interpretation and can be subjective in nature. In addition, in some cases, this type of imaging may indicate tumor recurrence, but in fact the abnormality turns out to be treatment effect. Depending on the type of tumor, surgical intervention can be highly invasive, with extensive recovery time.

A less invasive method to reliably identify tumor recurrence would be valuable to clinicians and their patients during evaluations following treatment and/or surgical resection of a tumor.

SUMMARY

The present disclosure is directed toward measurement of expression of one or both of an activating Natural Killer (NK) cell receptor and its ligand(s) on peripheral blood cells as a means to assess solid tumor burden. In particular, the present disclosure provides tools for assessing prognosis of a cancer patient having a solid tumor, recurrence of the solid tumor or risk thereof following reduction of the tumor, as well as tools for developing a treatment regime for the cancer patient.

Specifically the present disclosure provides methods for assessing recurrence of a solid tumor or risk thereof in a cancer patient, the method comprising: a) subjecting a post-treatment blood sample from the patient to a procedure for quantitation of expression of a NKG2D ligand, wherein the procedure comprises an antibody based technique or a nucleic acid based technique; and b) detecting an elevated level of the NKG2D ligand in the post-treatment blood sample as compared to a control blood sample, wherein the elevated level of expression is associated with recurrence of the solid tumor. In some embodiments, the cancer patient does not have a leukemia, a lymphoma or a myeloma. In some preferred embodiments, the blood sample is a peripheral blood mononuclear cell sample. In some embodiments, the methods comprises quantitation of one or both of a soluble form of the NKG2D ligand in serum derived from the blood sample, and a membrane-associated form of the NKG2D ligand in myeloid cells of the blood sample. In further embodiments, the methods comprises quantitation of expression of NKG2D on NK cells and CD8+ T cells of the blood sample. In some embodiments, the NKG2D ligand comprises one or more of the group consisting of MICA, MICB, ULBP1, ULBP2, ULBP3, ULBP4, ULBP5 and ULBP6. In some preferred embodiments, the NKG2D ligand comprises one or more of the group consisting of MICA, MICB, and ULBP1. In some embodiments, the solid tumor is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatocellular carcinoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioblastoma multiforme, astrocytoma, medulloblastoma, craniopharyngioma, ependymoma, pinealoma, hemangioblastoma, acoustic neuroma, oligodendroglioma, melanoma, neuroblastoma, and retinoblastoma. In some preferred embodiments, the solid tumor is selected from the group consisting of glioblastoma multiforme, hepatocellular carcinoma, prostate cancer, and breast cancer. In some embodiments, the control blood sample is a blood sample from a tumor-free subject or a blood sample from the patient at a time when tumor burden is known to be minimal (e.g., 1 month or so after tumor resection or cessation of cancer treatment upon cancer remission). In some embodiments, the methods further comprise: c) resuming treatment of the patient when the elevated level of expression is detected. In some preferred embodiments, the treatment comprises one or more of surgery, chemotherapy, radiation, and steroid therapy. In some embodiments, the treatment comprises chemotherapy with one or more of a TGF-beta inhibitor, a M-CSF inhibitor and a GM-CSF inhibitor. In some embodiments, the methods further comprise: a step before a) of obtaining the post-treatment blood sample from the patient. In some particularly preferred embodiments, the elevated level of expression is detected on CD11b-positive myeloid cells. In some preferred embodiments, the myeloid cells express one or both of CD45 and MHC class II. In some preferred embodiments, the MHC class II is HLA-DR. In some embodiments, the procedure for quantitation comprises an antibody-based technique. In some preferred embodiments, the antibody-based technique comprises a procedure selected from but not limited to flow cytometry, antibody microarray, ELISA, and Western blotting. In other embodiments, the procedure for quantitation comprises a nucleic-acid based technique. In some preferred embodiments, the nucleic acid based technique comprises a procedure selected from but not limited to RT-PCR, nucleic acid microarray, serial analysis of gene expression, massively parallel signature sequencing, and northern blotting.

Also provided by the present disclosure are kits for assessing prognosis of a cancer patient having a solid tumor, recurrence of a solid tumor in a cancer patient, or risk of recurrence of a solid tumor in a cancer patient, the kit comprising biomarker-specific reagents consisting essentially of: a NKG2D ligand-specific reagent; a first myeloid cell-reactive reagent, and a second myeloid cell-reactive reagent. In some embodiments, the first myeloid cell-reactive reagent and the second myeloid cell-reactive reagent are two different reagents selected from the group consisting of a CD11b-specific reagent, a CD45-specific reagent, a CD11a-specific reagent, a CD14-specific reagent, a CD16-specific reagent, a CD62L-specific reagent, a CD163-specific reagent, and a MHC class II-specific reagent. In some embodiments, the first myeloid cell-reactive reagent and the second myeloid cell-reactive reagent are a CD11b-specific reagent; and a CD45-specific reagent. In some embodiments, the first myeloid cell-reactive reagent and the second myeloid cell-reactive reagent are a CD11b-specific reagent; and a MHC class II-specific reagent. In some preferred embodiments, the MHC class II-specific reagent is a HLA-DR-specific reagent. In some embodiments, the NKG2D ligand-specific reagent comprises one or more of the group consisting of a MICA-specific reagent, a MICB-specific reagent, a ULBP1-specific reagent, a ULBP2-specific reagent, a ULBP3-specific reagent, a ULBP4-specific reagent, a ULBP5-specific reagent, and a ULBP6-specific reagent. In some preferred embodiments, the NKG2D ligand-specific reagent comprises one or more of the group consisting of a MICA-specific reagent, a MICB-specific reagent, and a ULBP-1-specific reagent. In some embodiments, the NKG2D ligand-specific reagent, and both of the myeloid cell-reactive reagents are antibodies. In other embodiments, the NKG2D ligand-specific reagent, and both of the myeloid cell-reactive reagents are nucleic acids. In some embodiments, the cancer patient does not have a leukemia, a lymphoma or a myeloma. In some preferred embodiments, the blood sample is a peripheral blood mononuclear cell sample.

Moreover the present disclosure provides methods for assessing prognosis of a cancer patient having a solid tumor, the method comprising: a) subjecting a pre-treatment blood sample from the patient to a procedure for quantitation of expression of a NKG2D ligand, wherein the procedure comprises an antibody based technique or a nucleic acid based technique; and b) detecting an elevated level of expression of the NKG2D ligand in the pre-treatment blood sample as compared to a control blood sample from a healthy subject, wherein the elevated level of expression is associated with a poor prognosis. In some embodiments, the patient does not have leukemia, lymphoma or myeloma. In some preferred embodiments, the blood sample is a peripheral blood mononuclear cell sample. In some embodiments, the NKG2D ligand comprises one or more of the group consisting of MICA, MICB, ULBP1, ULBP2, ULBP3, ULBP4, ULBP5 and ULBP6. In some preferred embodiments, the NKG2D ligand comprises one or more of the group consisting of MICA, MICB, and ULBP1. In some embodiments, the solid tumor is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatocellular carcinoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioblastoma multiforme, astrocytoma, medulloblastoma, craniopharyngioma, ependymoma, pinealoma, hemangioblastoma, acoustic neuroma, oligodendroglioma, melanoma, neuroblastoma, and retinoblastoma. In some preferred embodiments, the solid tumor is selected from the group consisting of glioblastoma multiforme, hepatocellular carcinoma, prostate cancer, and breast cancer. Some methods of the present disclosure further comprise: c) adopting an aggressive treatment regimen for the patient when the elevated level of expression is detected. Some methods of the present disclosure further comprise: a step before a) of obtaining the pre-treatment blood sample from the patient. In some preferred embodiments, the elevated level of expression is detected on CD11b-positive myeloid cells. In some preferred embodiments, the myeloid cells express one or both of CD45 and MHC class II. In some preferred embodiments, the MHC class II comprises HLA-DR.

BRIEF DESCRIPTION OF THE DRAWINGS

FIG. 1A provides histograms of CD3+, CD8+ cells from peripheral blood lymphocytes (PBL) and tumor infiltrating lymphocytes (TIL) of glioblastoma multiforme (GBM) and meningioma (MNG) patients. FIG. 1B provides the results of analyses of NKG2D expression on NK and CD8+ T cells of PBL from GBM patients before and after a significant surgical reduction in tumor burden. FIG. 1C provides MRI confirmation of the surgical reduction of tumor burden.

DEFINITIONS

Figure 1:
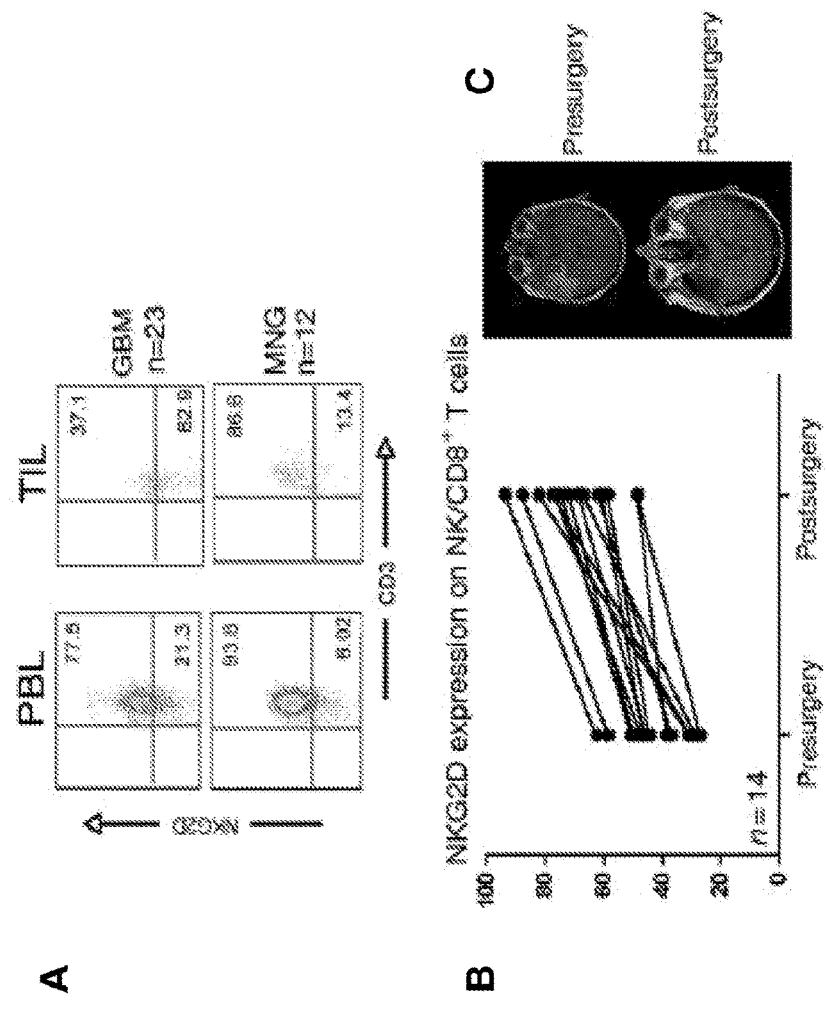
FIG. 1A-C illustrates that expression of the activating receptor NKG2D is decreased on CD8+ T cells in patients with glioblastoma multiforme.

To facilitate an understanding of the embodiments disclosed herein, a number of terms and phrases are defined below.

The terms "NKG2D," "NKG2-D," "D12S2489E," "KLRK1," and "killer cell lectin-like receptor subfamily K, member 1," as used herein refer to a human killer cell activating receptor gene, cDNA (e.g., Homo sapiens—GENBANK Accession No. NM_007360), and its gene product, as well as its mammalian counterparts. Preferred embodiments of the present disclosure comprise agents for measuring NKG2D protein or mRNA expression.

The terms "NKG2DL" and NKG2D ligand" when used in reference to human ligands refer to MICA, MICB, ULBP1, ULBP2, ULBP3, ULBP4, ULBP5 and ULBP6.

The term "elevated level of expression" as used herein refers to a level of expression (transcription or translation) of an antigen (such as a NKG2DL) in a test blood sample that is at least 1.1x greater than the level of expression of the antigen in a control blood sample. In some embodiments, an elevated level is at least 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 times greater.

As used herein, the term "solid tumor" refers to an abnormal mass of tissue that is typically devoid of cysts or liquid areas. Solid tumors may be benign (not cancer), or malignant (cancer). Different types of solid tumors are named for the type of cells that form them. Examples of solid tumors are sarcomas, carcinomas, and lymphomas. The term "solid tumor" is used to distinguish between a localized mass of tissue and leukemia. (cancers of the blood). "Sarcomas" are cancers arising from connective or supporting tissues such as bone or muscle. "Carcinomas" are cancers arising from glandular cells and epithelial cells, which line body tissues. "Lymphomas" are cancers of the lymphoid organs such as the lymph nodes, spleen, and thymus. As these cells occur in most tissues of the body, lymphomas may develop in a wide variety of organs. Exemplary solid tumors include but are not limited to sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatocellular carcinoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioblastoma multiforme, astrocytoma, medulloblastoma, craniopharyngioma, ependymoma, pinealoma, hemangioblastoma, acoustic neuroma, oligodendroglioma, melanoma, neuroblastoma, and retinoblastoma.

Aggressive treatment regime: A cancer treatment regime in which the emphasis is on killing and/or removing the cancer from the body as thoroughly as possible, to the possible detriment of patient comfort and/or safety. As compared to a conservative treatment regime, an aggressive treatment regime may, for example, use higher doses of anti-cancer therapeutics, higher total treatment times, and more radical surgeries.

Conservative treatment regime: A cancer treatment regime in which efforts are made to kill and/or remove the cancer from the body, but which also heavily takes into account patient comfort and/or safety. As compared to an aggressive treatment regime, a conservative treatment regime may, for example, use lower doses of anti-cancer therapeutics, lower total treatment times, and less radical surgeries.

Immuno-based/Antibody-based: Any technique that involves the use of an antibody to detect an antigen Immuno-based techniques include immunostaining, ELISA, antibody microarray, flow cytometry, and Western blotting.

Nucleic acid-based: Any technique that involves the use of a nucleic acid to detect another nucleic acid. Nucleic acid includes both DNA and RNA. Nucleic acid-based techniques include nucleic acid microarray, RT-PCR, northern blotting, nuclease protection assays, and in situ hybridization.

DETAILED DESCRIPTION

The present disclosure is directed toward measurement of expression of one or both of an activating NK cell receptor and its ligand(s) on peripheral blood cells as a means to assess solid tumor burden. In particular, the present disclosure provides tools for assessing cancer recurrence following reduction of a solid tumor, and for developing a treatment regime for a cancer patient.

The tumor microenvironment is known to be highly immunosuppressive. Many specific proteins have been identified that prevent adequate activation of infiltrating immune cells, such as CTLA-4 and B7-H1. One such immune cell is the Natural Killer (NK) cell, which secretes inflammatory cytokines and kills transformed cells. There is significant evidence supporting the involvement of NK cells in the elimination of tumor cells in the early stages of tumor development. One major mechanism of NK cell activation is through the NKG2D receptor. Activated NK cells reject NKG2D ligand-expressing tumors in mouse models, and human NK cells lyse tumor cells through NKG2D-mediated activation.

It is not known how tumor cells establish a method to escape recognition by immune cells, resulting in solid tumor development. However, there is extensive recruitment of myeloid cells, which is believed to promote angiogenesis and metastasis, and prevent immune cell activation. Using cellular and molecular biological techniques, the crosstalk between tumor cells, the myeloid cells and NK cells in patients with glioblastoma was studied during development of the present disclosure.

As described herein and illustrated in the accompanying figures, a variety of human cancers induce the expression of NKG2D ligands on circulating myeloid cells. In patients with glioblastoma (GBM), a deadly brain tumor, NKG2D ligand expression on myeloid cells is independent of steroid treatment, surgical intervention, and chemotherapy. Transwell assays indicate that myeloid cell expression of NKG2D ligands is a consequence of a soluble factor or factors produced by tumor cells. NKG2D ligand expression on circulating myeloid cells is sufficient to induce inflammatory responses by NK cells that are dependent on NKG2D.

Several important observations were made during development of the present disclosure. Tumors in GBM patients express NKG2D ligands, and are infiltrated with NK cells and myeloid cells. Circulating myeloid cells in GBM patients express NKG2D ligands. NKG2D ligand expression is independent of steroid treatment, surgical intervention, radiation and chemotherapy. IL-2 activated NK cells eliminate NKG2D ligand expressing monocytes. Soluble factors secreted by tumor cells are sufficient to induce NKG2D ligand expression on monocytes. Soluble factors that induce NKG2D ligands can be denatured and are larger than 10 kDa, indicating that they are proteins. M-CSF and GM-CSF, but not TGF-beta, IL-2, IFN-gamma, VEGF and EGF, induce NKG2D ligand expression on NKG2D ligand negative monocytes. M-CSF is detectable in GBM patient sera and tumor cell supernatants. M-CSF receptor is increased on CD11b-positive cells in GBM patients.

Figure 11:
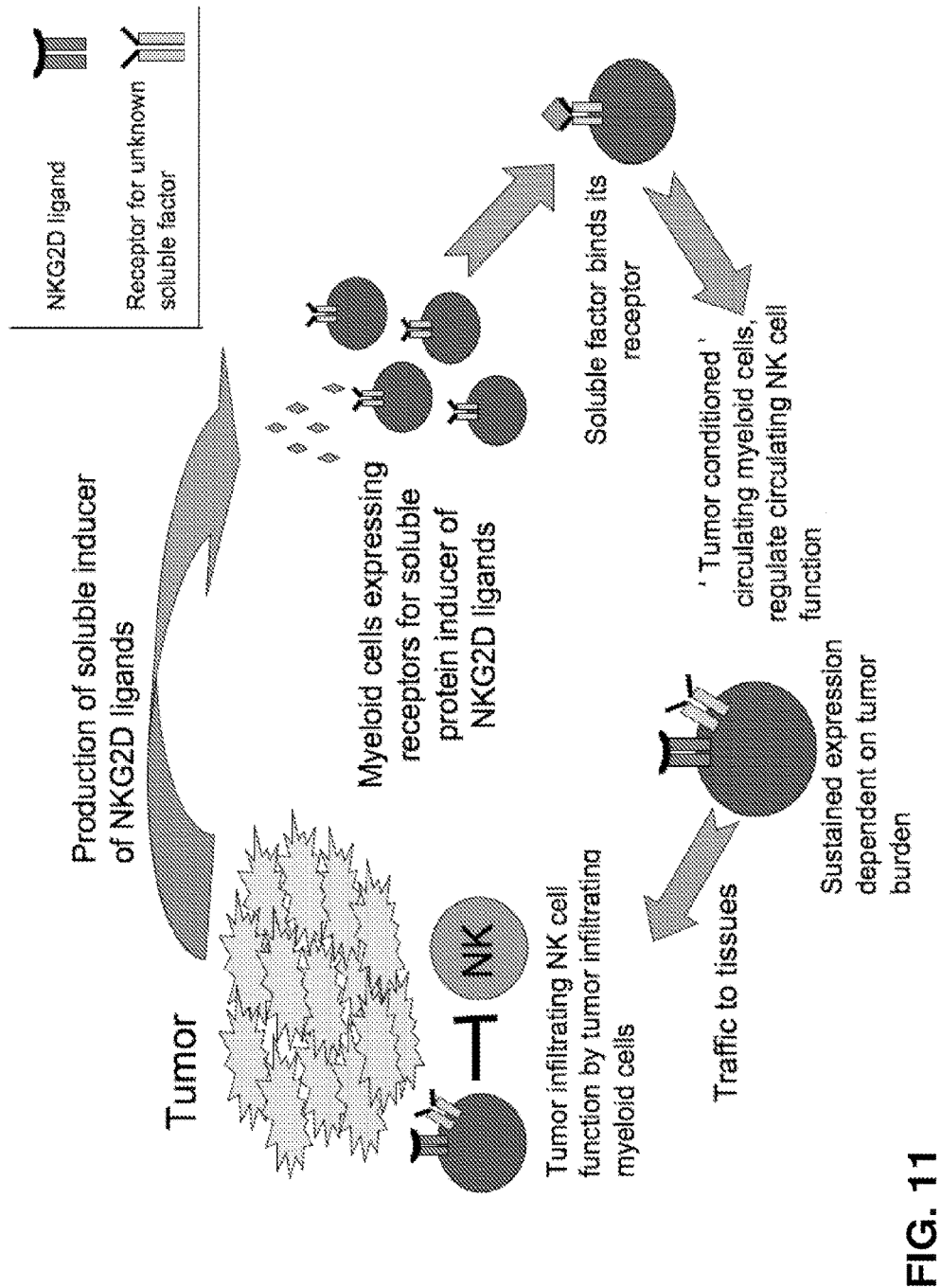
FIG. 11 provides a model of NKG2D ligand induction on circulating and tumor infiltrating myeloid cells.

FIG. 11 provides a model of NKG2D ligand induction on circulating and tumor infiltrating myeloid cells, which was determined during development of the present disclosure. Glioblastoma cells produce a soluble protein whose receptor is expressed by circulating myeloid cells. Receptor ligation results in induction of NKG2D ligands, which impacts NK cell activation and target cell lysis in circulation. Tumor resection is sufficient to reduce NKG2D ligand expression because the inducing protein is tumor-derived. Circulating myeloid cells are recruited to the tumor site, where NKG2D ligand expression impairs NK cell lysis of target cells. Thus myeloid expression of NKG2D ligands provides novel biomarker(s) of solid tumor burden. Moreover, the functional consequences of this expression provides novel target for improving immunotherapy of some solid tumors.

Prognostic and Diagnostic Methods

In one embodiment, cancer patients with a post-treatment blood sample with an elevated level of expression of a NKG2D ligand (one or more of MICA, MICB, ULBP1, ULBP2, ULBP3, ULBP4, ULBP5 and ULBP6) are identified as being at a greater risk for cancer metastasis and/or relapse (solid tumor recurrence), as compared to cancer patients with a post-treatment blood sample with a level of expression of the NKG2D ligand (one or more of MICA, MICB, ULBP1, ULBP2, ULBP3, ULBP4, ULBP5 and ULBP6) that is comparable to a blood sample from a control subject that is free of solid tumors. In some embodiments, the cancer patient is a patient having or having had a solid tumor selected from the group consisting of glioblastoma multiforme, hepatocellular carcinoma, prostate cancer and breast cancer, and the NKG2D ligand comprises one or more of MICA, MICB and ULBP1

In one embodiment, threshold levels of each marker are established to define an 'elevated' level of expression of the marker. Depending on the technique used and the marker examined, different values may be used to define an 'elevated' level of expression of the marker. In order to define an 'elevated' level of expression of a marker, statistical analysis such as random forest clustering may be used in order to identify optimum threshold levels.

A. Antibody Based Methods

In some embodiments, an elevated level of expression of a NKG2D ligand (one or more of MICA, MICB, ULBP1, ULBP2, ULBP3, ULBP4, ULBP5 and ULBP6) in a post-treatment blood sample from a cancer patient is determined by using antibody-based methods to determine the levels of each biomarker protein in the blood sample. Antibody-based methods include various techniques that involve the recognition of a NKG2D ligand (one or more of MICA, MICB, ULBP1, ULBP2, ULBP3, ULBP4, ULBP5 and ULBP6) using specific antibodies. For most techniques, monoclonal antibodies are used. However, for some techniques polyclonal antibodies can be used. Commonly used antibody-based techniques to detect the level of one or more proteins in a sample include flow cytometry, antibody microarray, ELISA, and Western blotting.

Immunohistochemistry. Immunohistochemistry is the general process of determining the location and/or approximate level of one or more antigens in a tissue sample using antibodies directed against the antigens of interest. Typically, a thin slice of tumor tissue sample is cut from a larger tumor sample and mounted onto a slide, followed by treating the slice of tumor tissue with one or more reagents (including antibodies) to detect the antigens of interest Immunohistochemistry can also be performed on tissue slices that are not mounted on a slide. In some instances, formalin-fixed and/or paraffin-embedded tissue samples are used for immunohistochemistry. Paraffinized samples can also be deparaffinized in order retrieve antigenicity of proteins.

During immunohistochemistry, antibody-antigen interactions can be detected through various mechanisms, including conjugating the antibody to an enzyme that can catalyze a color-producing reaction, such as a peroxidase, or conjugating the antibody to a fluorophore. A fluorophore is a molecule that will absorb energy at a specific wavelength and release energy at a different specific wavelength, e.g. fluorescein. The typical immunohistochemistry process involves treating first treating the thin tissue sample with blocking solution to reduce nonspecific background staining, followed by exposing the tissue sample the antibody or antibodies of interest, washing the tissue sample, and then visualizing the antibody-antigen complexes of interest.

Flow Cytometry. To analyze tumor samples by flow cytometry, the tumor sample is processed to separate the tumor into individual cells. The cells are incubated with fluorophore-tagged antibodies of interest, and the collection of cells is processed through a flow cytometer. The flow cytometer uses different wavelengths of light to excite and detect different fluorophores. By analyzing a collection of cells from a tumor sample that have been incubated with fluorophore-tagged antibodies of interest, a measurement of level of the different antigens of interest in the tumor sample can be obtained.

Antibody Microarray. The general process for an antibody microarray is to bind a collection of antibodies against antigens of interest to a fixed surface (to create the microarray), to incubate the microarray with a sample that may contain the antigen(s) of interest, and then to add one or more reagents that allow for the detection of antibody microarray-bound antigens of interest. For antibody microarray analysis, a tumor sample is prepared by a homogenization technique, which eliminates large tumor particles which could interfere with the function of the antibody microarray, but that preserves the integrity of the antigens of interest. Reagents that can be used for detection of antibody microarray-bound antigens of interest include fluorophore or enzyme-tagged antibodies.

Enzyme-linked Immunosorbent Assay (ELISA). To detect protein levels in a sample by ELISA, what is commonly known as a 'Sandwich ELISA' is performed. For a Sandwich ELISA, antibodies against an antigen of interest are linked to a surface. The surface-linked antibodies are exposed to a non-specific blocking agent, and then they are incubated with a sample containing the antigens of interest (e.g. in this case, a tumor sample or patient sera). After incubation, the surfaces are washed to remove unbound material, and then antibodies that bind to another epitope on the antigen of interest are added. These antibodies can be directly linked to a fluorophore or an enzyme to allow for their detection, or a secondary antibody linked to a fluorophore or an enzyme can be used to detect these antibodies. Through this technique, the level of one or more antigens in a sample can be determined.

Western Blotting. For Western blotting, a tumor sample of interest is homogenized, and a sample of the tumor is separated by polyacrylamide gel electrophoresis. The electrophoresis step separates proteins in the sample applied to the gel, and the proteins in the gel are next transferred to a membrane. Typically, PVDF or nitrocellulose membranes are used. After transferring proteins from the gel to the membrane, the membrane is treated with a non-specific blocking agent, and then incubated with antibodies against an antigen of interest. After incubation of the sample with the specific antibodies, the membrane is washed, and then treated with a secondary antibody that binds to the specific antibody. The secondary antibody is typically linked to an enzyme, which can be used to create a reaction to detect the location and approximate level of the antigen of interest on the membrane.

B. Nucleic Acid-Based Methods

In other embodiments, an elevated level of expression of a NKG2D ligand (one or more of MICA, MICB, ULBP1, ULBP2, ULBP3, ULBP4, ULBP5 and ULBP6) in a post-treatment blood sample from a cancer patient is determined by using nucleic acid-based methods to determine the levels of each biomarker mRNA in the tumor sample or blood sample. In general, methods of mRNA level and gene expression profiling can be divided into two large groups: methods based on hybridization analysis of polynucleotides, and methods based on sequencing of polynucleotides. The most commonly used methods known in the art for the quantification of mRNA expression in a sample include Northern blotting (Parker and Barnes, Methods in Molecular Biology 106:247-283, 1999); RNAse protection assays (Hod, Biotechniques 13:852-854, 1992); and quantitative or semi-quantitative reverse transcription polymerase chain reaction (RT-PCR) (Weis et al., *Trends in Genetics* 8:263-264, 1992). Representative methods for sequencing-based gene expression analysis include Serial Analysis of Gene Expression (SAGE), and gene expression analysis by massively parallel signature sequencing (MPSS).

RT-PCR. Of the techniques listed above, the most sensitive and most flexible quantitative method is RT-PCR, which can be used to compare mRNA levels in different sample populations, in normal and tumor tissues or blood, with or without drug treatment, to characterize patterns of gene expression, to discriminate between closely related mRNAs, and to analyze RNA structure.

The first step is the isolation of mRNA from a target sample. The starting material is typically total RNA isolated from human tumors or tumor cell lines or blood, and corresponding normal tissues or cell lines or blood, respectively. Thus, RNA can be isolated from a variety of primary tumors, including breast, lung, colon, prostate, brain, liver, kidney, pancreas, spleen, thymus, testis, ovary, uterus, etc., tumor, or tumor cell lines, with pooled DNA from healthy donors being used as a control. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin-embedded tissues are disclosed, for example, in Rupp and Locker, *Lab Invest.* 56:A (1987), and De Andres et al., *BioTechniques* 18:42044 (1995). In particular, RNA isolation can be performed using purification kit, buffer set and protease from commercial manufacturers, such as Qiagen, according to the manufacturer's instructions. Other commercially available RNA isolation kits include MASTERPURE™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor or blood cells can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TAQMAN® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ SEQUENCE DETECTION SYSTEM™. The system consists of a thermocycler, laser, charge-coupled device (CCD), camera and computer. The system amplifies samples in a 96-well format on a thermocycler. During amplification, laser-induced fluorescent signal is detected at the CCD. The system includes software for running the instrument and for analyzing the data.

5'-Nuclease assay data are initially expressed as CT, or the threshold cycle. As discussed above, fluorescence values are recorded during every cycle and represent the amount of product amplified to that point in the amplification reaction. The point when the fluorescent signal is first recorded as statistically significant is the threshold cycle ($C_T$).

To minimize errors and the effect of sample-to-sample variation, RT-PCR is usually performed using one or more reference genes as internal standards. The ideal internal standard is expressed at a constant level among different tissues. RNAs most frequently used to normalize patterns of gene expression are mRNAs for the housekeeping genes glyceraldehyde-3-phosphate-dehydrogenase (GAPDH) and β-actin (ACTB).

A more recent variation of the RT-PCR technique is the real-time quantitative PCR, which measures PCR product accumulation through a dual-labeled fluorigenic probe (i.e., TAQMAN® probe). Real-time PCR is compatible both with quantitative competitive PCR, where internal competitor for each target sequence is used for normalization, and with quantitative comparative PCR using a normalization gene contained within the sample, or a housekeeping gene for RT-PCR (for further details see, e.g. Held et al., *Genome Research* 6:986-994, 1996).

The steps of a representative protocol for profiling gene expression using fixed, paraffin-embedded tissues as the RNA source, including mRNA isolation, purification, primer extension and amplification are given in various published journal articles (for example, Godfrey et al., J. Molec. Diagnostics 2: 84-91, 2000; Specht et al., Am. J. Pathol. 158: 419-29, 2001; and Cronin et al., Am J Pathol 164:35-42, 2004). Briefly, a representative process starts with cutting about 10 µm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR.

Microarrays. Differential gene expression can also be identified, or confirmed using the microarray technique. Thus, the expression profile of breast cancer-associated genes can be measured in either fresh or paraffin-embedded tumor tissue, using microarray technology. In this method, polynucleotide sequences of interest (including cDNAs and oligonucleotides) are plated, or arrayed, on a microchip substrate. The arrayed sequences are then hybridized with specific probes from cells or tissues of interest. Just as in the RT-PCR method, the source of mRNA typically is total RNA isolated from human tumors or tumor cell lines, and corresponding normal tissues or cell lines. Thus RNA can be isolated from a variety of primary tumors or tumor cell lines or blood. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, the microarrayed genes are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93:106-149, 1996). Microarray analysis can be performed by commercially available equipment, following manufacturer's protocols, such as by using the Affymetrix GenChip technology, or Incyte's microarray technology.

Serial Analysis of Gene Expression (SAGE). Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, which can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., *Science* 270:484-487 (1995); and Velculescu et al., *Cell* 88:243-51 (1997).

Gene Expression Analysis by Massively Parallel Signature Sequencing (MPSS). This method (described by Brenner et al., *Nature Biotechnology* 18:630-634, 2000), is a sequencing approach that combines non-gel-based signature sequencing with in vitro cloning of millions of templates on separate 5 µm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/$cm^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

Treatment Methods

In yet another embodiment, determination of an elevated level of expression of a NKG2D ligand (one or more of MICA, MICB, ULBP1, ULBP2, ULBP3, ULBP4, ULBP5 and ULBP6) in post-treatment blood sample from a cancer patient as compared to a control blood sample, resuming a cancer treatment regime for the cancer patient is indicated. For instance, in some embodiments, upon detection of an elevated level of expression of a NKG2D ligand (one or more of MICA, MICB, ULBP1, ULBP2, ULBP3, ULBP4, ULBP5 and ULBP6) in post-treatment blood sample from a cancer patient, further surgery, chemotherapy, radiation, and/or steroid treatment is indicated.

Kits

In another embodiment, a kit comprising biomarker-specific reagents consisting essentially of reagents capable of detecting NKG2D ligands, CD11b and CD45 in a peripheral blood sample is provided. Reagents capable of detecting NKG2D ligand (NKG2DL), CD11b and CD45 molecules include but are not limited to anti-NKG2DL, anti-CD11b, and anti-CD45 antibodies, and nucleic acids capable of forming duplexes with NKG2DL, CD11b, and CD45 mRNA, respectively. Nucleic acids capable of forming duplexes with CD4, CD8 or CD68 mRNA include DNA or RNA sequences which are complementary to the respective mRNA sequence. Reagents capable of detecting a NKG2D ligand, CD11b and CD45 molecules are also typically directly or indirectly linked to a molecule such as a fluorophore or an enzyme which can catalyze detectable reaction, in order to indicate the binding of the reagents to their respective targets. In some embodiments, the NKG2D ligand comprises one or more of MICA, MICB, ULBP1, ULBP2, ULBP3, ULBP4, ULBP5 and ULBP6, while in some preferred embodiments, the NKG2D ligand (NKG2DL) comprises one or more of the group consisting of MICA, MICB, ULBP1, ULBP2, ULBP3, ULBP4, ULBP5, and ULBP6.

EXPERIMENTAL

The present disclosure is described in further detail in the following examples, which are not in any way intended to limit the scope of the disclosure as claimed. The attached figures are meant to be considered as integral parts of the specification and description of the disclosure. The following examples are offered to illustrate, but not to limit the claimed disclosure.

In the experimental disclosure which follows, the following abbreviations apply: M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml and mL (milliliters); µl and µL (microliters); cm (centimeters); mm (millimeters); um (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); H₂O (water); dH₂O (deionized water); aa (amino acid); by (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); OD (optical density); PCR (polymerase chain reaction); RT-PCR (reverse transcription PCR); CTL (cytotoxic T lymphocyte); Th (helper T lymphocyte); NK (natural killer cell); PBL (peripheral blood lymphocytes); PBMC (peripheral blood mononuclear cells; TIL (tumor-infiltrating lymphocytes); GBM (glioblastoma multiforme); and MNG (meningioma).

Example 1

Biomarker Expression on Peripheral Blood Mononuclear Cells (PBMC) from Cancer Patients This example provides a description of the materials and methods and results of analyses of the role of NKG2D ligands on myeloid cell-natural killer cell cross-talk in patients with solid tumors.

Materials and Methods

Peripheral Blood and Tumor-Infiltrating Lymphocyte Isolation. Peripheral blood lymphocytes (PBLs) were isolated by Ficoll centrifugation. Tumor-infiltrating lymphocytes (TILs) were isolated with a three-step density gradient as described previously (Ford et al., J Immunol, 154:4309-4321, 1995).

Patients. Peripheral blood lymphocytes were isolated from recurrent glioblastoma multiforme (GBM) patients immediately prior to tumor resection and again 34.8 (SD 5.6) days (e.g., about one month post-treatment) following gross total resection. No patients had tumor recurrence at the time of the postsurgical blood draw. Patients were not on steroids at the time of blood draws.

Flow Cytometry. Fc receptors (FcRs) were blocked using FcR blocking reagent (Miltenyi Biotec) and stained with the indicated antibodies to HLA-DR APC, CD11b PeCy7, ULBP-1 FITC and MICA/B PE, or isotype-matched control antibodies (BD, eBioscience or R&D Systems). Samples were acquired using a FACSCalibur (BD) and analyzed using FlowJo software (TreeStar).

Immunofluorescence. Frozen tissues of 10 micron sections were incubated with monoclonal antibodies to MICA (clone M673) and MICB (clone M362) or ULBP1 (clone M295), ULBP-2 (clone M310), ULBP-3 (clone M551), generously provided by Amgen, Inc. Antibody binding was detected by using fluorescently conjugated anti-mouse IgG and IgM antibodies (Abcam).

Cytotoxicity. Natural Killer cells were isolated with an NK cell selection kit (StemCell Technologies, Inc.) and activated overnight with 1000 U/mL recombinant IL-2 (NIH). Natural Killer cells were cultured at a 1:1 ratio with SF767 or U87 glioma cells in the presence of PE-conjugated anti-CD107 for 3 h.

Enzyme-Linked Immunosorbent Assay (ELISA). Amounts of soluble MICB in sera were determined using the MICB ELISA Duoset (R&D Systems) according the manufacturer's instructions.

Reverse Transcribed-Quantitative Polymerase Chain Reaction (RT-PCR). Whole cell mRNA was reverse transcribed, and quantitative polymerase chain reaction was performed using the following primers: NKG2D: forward NKG2D, 5'-CAC AGC TGG GAG ATG AGT GA-3' (SEQ ID NO:1), and reverse NKG2D 5'-CTA CAG CGA TGA AGC AGC AG-3' (SEQ ID NO:2); MICA: forward MICA, 5'-ACA ATG CCC CAG TCC TCC AGA-3' (SEQ ID NO:3), and reverse MICA, 5'-ATT TTA GAT ATC GCC GTA GTT CCT-3' (SEQ ID NO:4); MICB: forward MICB 5'-TGA GCC CCA CAG TCT TCG TTA C-3' (SEQ ID NO:5), and reverse MICB, 5'-TGC CCT GCG TTT CTG CCT GTC ATA-3' (SEQ ID NO:6); ULBP1: forward ULBP1, 5'-TGC AGG CCA GGA TGT CTT GT-3' (SEQ ID NO:7), and reverse ULBP1, 5'-CAT CCC TGT TCT TCT CCC ACT TC-3' (SEQ ID NO:8); ULBP2: forward ULBP2, 5'-CCC TGG GGA AGA AAC TAA ATG TC-3' (SEQ ID NO:9), and reverse ULBP2, 5'-ACT GAA CTG CCA AGA TCC ACT GCT-3' (SEQ ID NO:10); ULBP3: forward ULBP3 5'-AGA TGC CTG GGG AAA ACA ACT-3' (SEQ ID NO:11), and reverse ULBP3 5'-GTA TCC ATC GCC TTC ACA CTC ACA-3' (SEQ ID NO:12); ULBP4: forward ULBP4 5'-TAT GTC GAC CTC CAC AGT ATG CGA AGA-3' (SEQ ID NO:13), and reverse ULBP4 5'-GTA TCC ATC GGC TTC ACA CTC ACA-3' (SEQ ID NO:14); and HPRT: forward HPRT 5'-GAC CAG TCA ACA GGG GAC AT-3' (SEQ ID NO:15), and reverse HPRT 5'-CTT GCG ACC TTG ACC ATC TT-3' (SEQ ID NO:16). Data were collected and analyzed using the iQ5 Real Time System (BioRad).

Statistical Analysis. A two-tailed Student t test was used to compare glioblastoma multiforme (GBM) and meningioma (MNG) groups of patients. Statistics Q2 were done using Prism software (GraphPad Software, Inc.).

Results and Discussion

Figure 2:
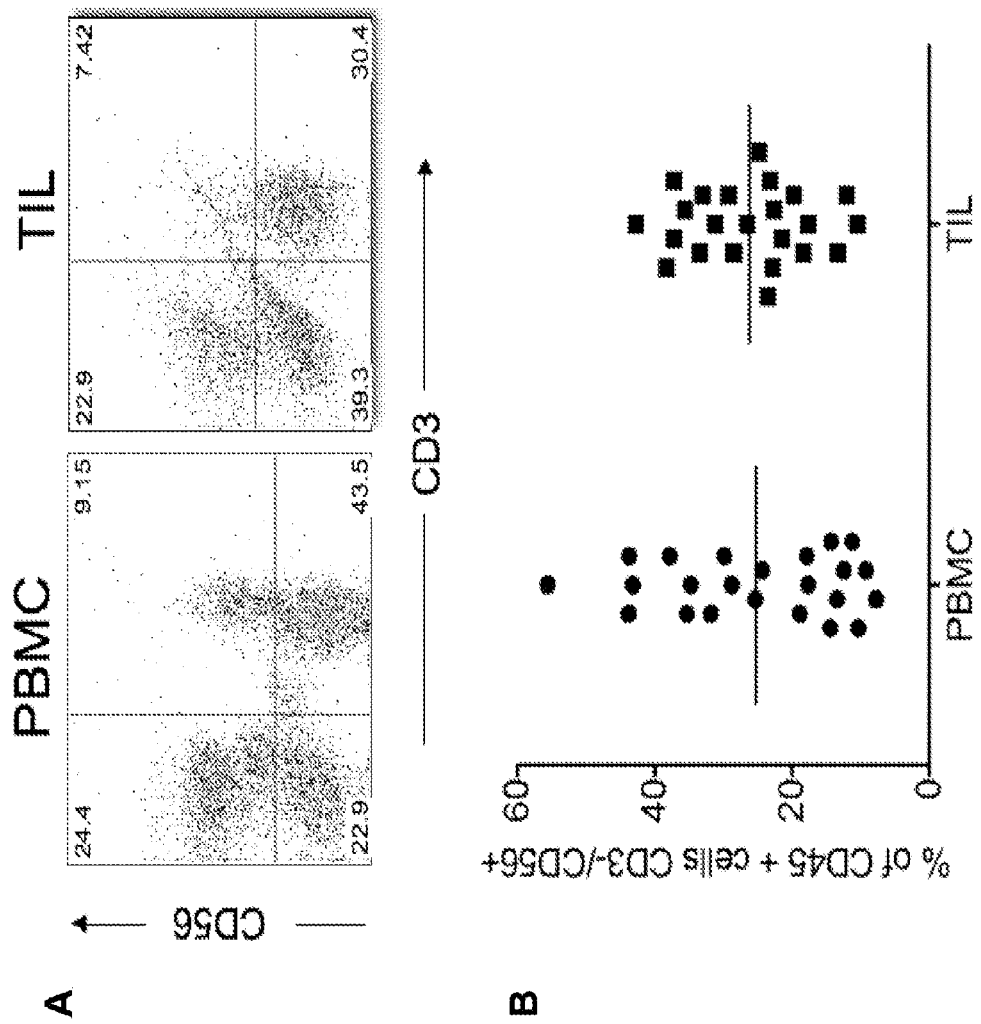
FIG. 2A-B illustrates the phenotype of peripheral blood mononuclear cells (PBMC) and tumor infiltrating lymphocytes (TIL) isolated from glioblastoma multiforme (GBM) patients at the time of tumor resection. Circulating PBMC and TIL were stained using fluorescently conjugated antibodies to CD45, CD3, and CD56. NK cells were defined as CD45+, CD3−, CD56+ cells. Plots represent gated populations of CD45 positive cells.

Healthy brain tissue does not have a substantial infiltration of circulating leukocytes, relying instead on local immune cells such as microglia to initiate local immune responses. Circulating peripheral blood mononuclear cells (PBMC) isolated from whole blood and tumor-infiltrating leukocytes (TIL) were isolated from 1 gram of tumor tissue from glioblastoma multiforme (GBM) patients. Between $6 \times 10^6$ and $1.4 \times 10^7$ CD45-positive cells were recovered from one gram of GBM tumor tissue. Of the CD45+ cells (leukocytes), a range of CD56+, CD3− NK cells were recovered, reflecting the increased percentage of circulating NK cells found in these patients (FIG. 2B), with a mean percentage of 25.3 (+/−2.87) in PBMC and 26.25 (+/−1.85) in TIL.

Successful immunotherapy is predicated upon effective activation, trafficking, and tumor cell recognition followed by tumor cell lysis mediated by immune effector cells. In patients with glioblastoma multiforme (GBM), it is especially important to avoid nonspecific tissue damage and autoimmune responses that can be associated with other types of immunotherapy (Hodi, Clin Cancer Res, 13:5238-5242, 2007). While monitoring patients before and after surgical resection of a recurrent GBM, expression of the activating receptor NKG2D was repeatedly observed to be diminished on the surface of both CD8+ T cells and NK cells (n=23) when compared with those isolated from patients with meningioma or other benign tumors (n=12) as shown in FIG. 1A, indicative of a systemic impact on these lymphocyte populations by tumor burden. This impaired expression was more pronounced in tumor-infiltrating CD8+ T cells when compared with circulating CD8+ T cells isolated from the same patient. Following tumor resection, the frequency of circulating NK cells and CD8+ T cells expressing NKG2D in the GBM patients increased from an average of 43.0% to 70.1% (P<0.01), which correlated with decreased tumor burden as shown in FIG. 1B and FIG. 1C. Together, these data indicate that in patients with GBM, tumor cells and/or the factors that they secrete impair expression of NKG2D on the surface of effector lymphocytes, thereby impairing the function of these immune effector cells. Cell surface levels of NKG2D can be modulated by soluble NKG2D ligands (Groh et al., Nature, 419:734-738, 2002) or through TGF-beta inhibition of NKG2D transcription (Castriconi et al., Proc Natl Acad Sci USA, 100:4120-4125, 2003; and Friese et al., Caner Res, 64:7596-7603, 2004).

Having confirmed the presence of NK cells in tumor tissue, whether tumor cells could be targets for activated NK cells as a result of NKG2D ligand expression was assessed. Because several studies have demonstrated NKG2D ligand expression by tumor cells in patients with cancer, expression of NKG2D ligands in vivo on GBM tumor cells was analyzed. The known ligands are the MHC class I-like molecules MICA and MICB, and the ULBP1, ULBP2, ULBP3, ULBP4, ULBP5, and ULBP6 proteins. Despite their structural diversity, ligation of NKG2D with any one of the ligands is sufficient to activate NK cells and facilitate target cell lysis (Cosman et al., Immunity, 14:123-133, 2001; and Steinle et al., Immunogenetics, 53:279-287, 2001). NKG2D ligand expression functions as an indication of cellular stress to the innate and adaptive immune systems, including expression by transformed or virally infected cells, but they are not expressed in healthy, nonmalignant tissues of adults. During development of the present disclosure, 10 of 11 GBM specimens were found to express MICA or MICB and ULBP1 or 2 by immunofluorescence using cocktails containing monoclonal antibodies to either MICA (clone M637) and MICB (clone M362) or ULBP-1 (clone M295) and ULBP-2 (clone M310), whereas tissues isolated from meningioma patients did not (0 of 11). ULBP-3 (clone M551) was not detected in either GBM tissues or MNG tissues.

To independently confirm the expression of the NKG2D ligands, single cell suspensions of GBM tissues were analyzed by flow cytometry. MICA/B (clone 6D4, reactive to both MICA and MICB) and ULBP-1 (clone 170818) were found to be expressed by MHC class I-positive, CD45-negative tumor cells. A majority of GBM patients expressed both MICA/B and ULBP-1 (88.9%, n=18), whereas very few of MNG specimens expressed either MICA or MICB, but no ULBP-1 (8.3%, n=12). A small subset (23.5%, n=17) of GBM patient tumor cells also expressed ULBP-2 by flow cytometry. Neither GBM nor MNG cells had detectable expression of ULBP-3 or ULBP-4, but were not tested for expression of ULBP-5 and ULBP-6. To ensure that the expression detected was not because of nonspecific antibody binding, tumor cell mRNA was analysed. MICA, MICB, ULBP1, and ULBP2 transcripts were detected in primary GBM tumor cells. Thus, the expression at the mRNA level confirmed the expression of MIC and ULBP-1 in tumor cells isolated from GBM patients.

Figure 3:
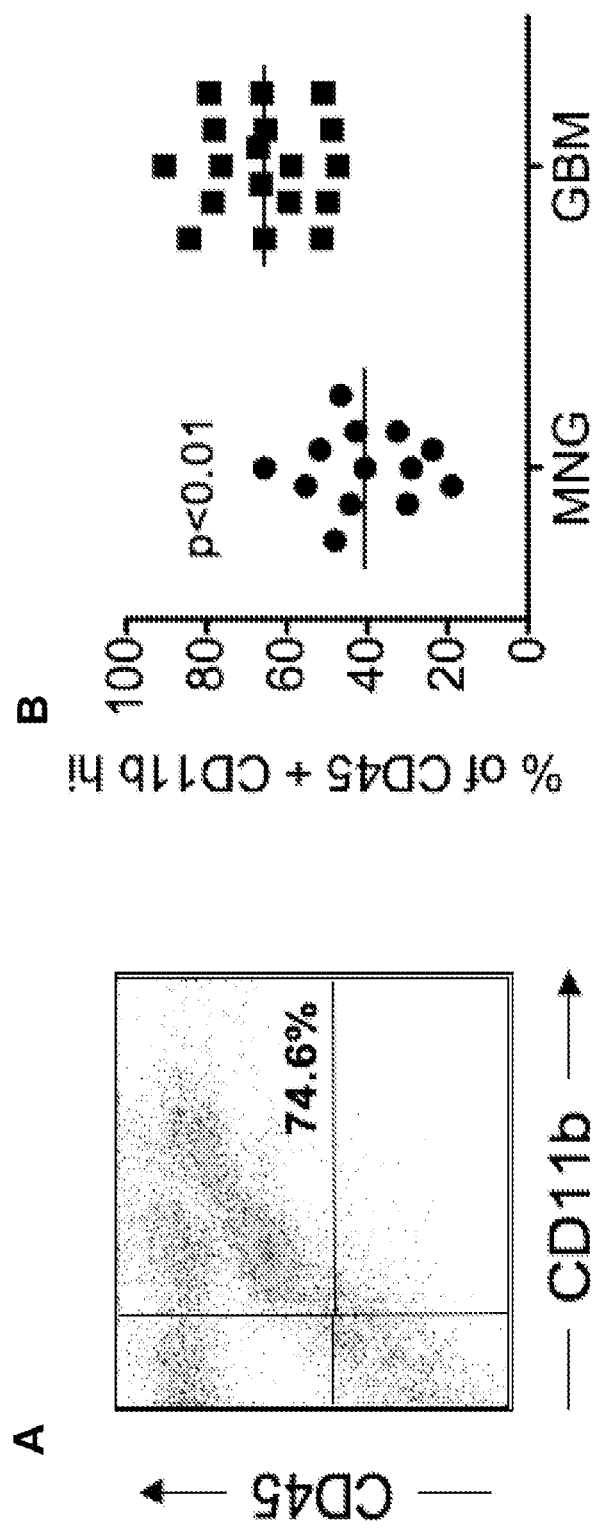
FIG. 3A-B illustrates that patients with GBM have increased myeloid cell infiltration of the tumor. Tumor-infiltrating leukocytes were isolated from patients with MNG (MNG, n=13) or GBM (GBM, n=18) and stained for CD45 (LCA) and CD11b and analyzed by flow cytometry to identify infiltrating myeloid cells.

Despite the robust expression of NKG2D ligands, tumor cells persist in vivo, indicating that NK cells are either not sufficiently activated to lyse tumor cells or can not access NKG2D ligand-expressing tumor cells. Nonetheless an understanding of the mechanism is not necessary in order to make or use the present disclosure. Previous studies suggest that the recruitment of myeloid cells to the tumor site protects the tumor from lysis by cytotoxic cells. As seen in other types of tumors, the most prevalent non-tumor cell type found infiltrating tumors in GBM patients is a population of myeloid cells, as defined by CD45 and CD11b expression. A mean of 65.86% (n=18) of CD45-positive cells among tumor-infiltrating leukocytes in GBM patients were found to be CD11b high, as compared to 40.79% (n=13, p<0.01) in patients with MNG (FIG. 3B). Recent studies suggest that soluble factors or reactive oxygen species secreted by tumor-associated myeloid cells can suppress local immune responses to tumor cells.

Figure 4:
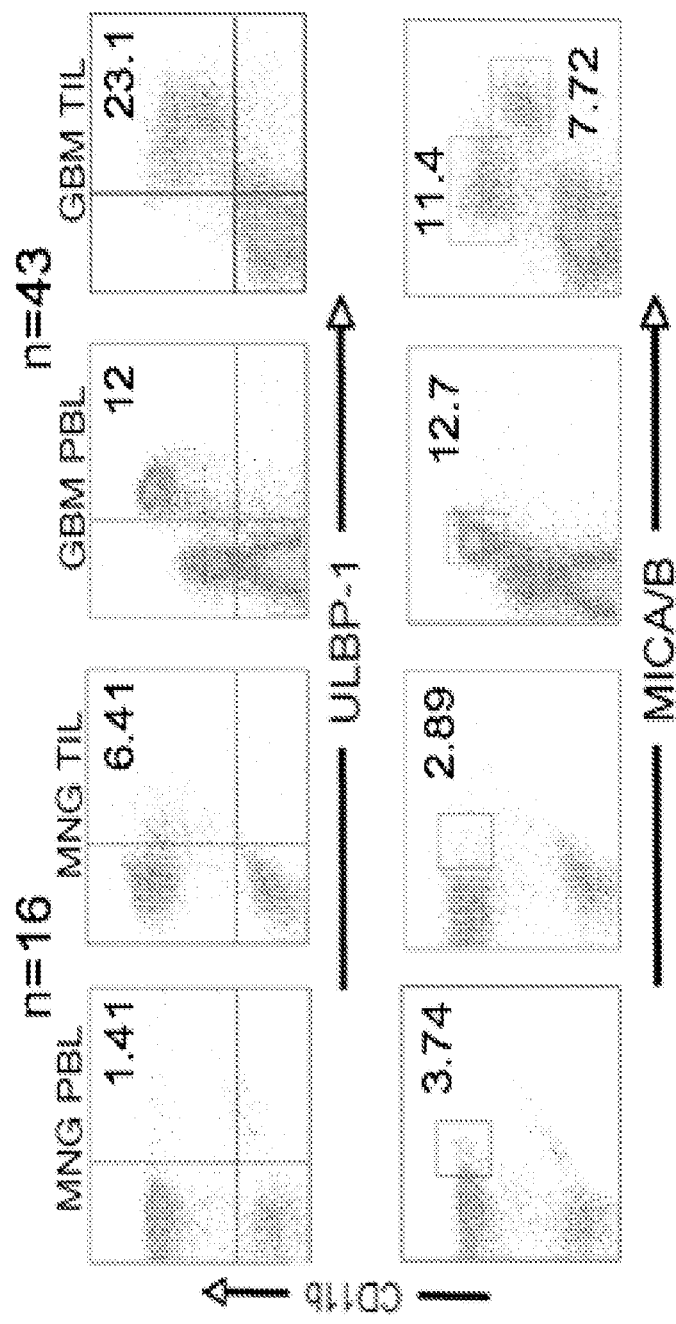
FIG. 4 illustrates that circulating and tumor infiltrating myeloid cells express the NKG2D ligands MICA/B and ULBP-1. Peripheral blood leukocytes (PBL) and tumor infiltrating leukocytes (TIL) isolated from patients with GBM or MNG were stained with fluorescently conjugated antibodies to CD45, CD11b, MICA/B, and ULBP-1. Plots show CD45-gated cells.

While evaluating the phenotype of myeloid cells in GBM patients, surprisingly circulating myeloid cells were found to express at least two of the activating ligands for NKG2D using an antibody that recognizes both MICA and MICB, as well as a monoclonal antibody to ULBP-1 (FIG. 4, n=43). In contrast, patients with MNG (n=16) do not express NKG2D ligands on either circulating or tumor-infiltrating myeloid cells.

Figure 5:
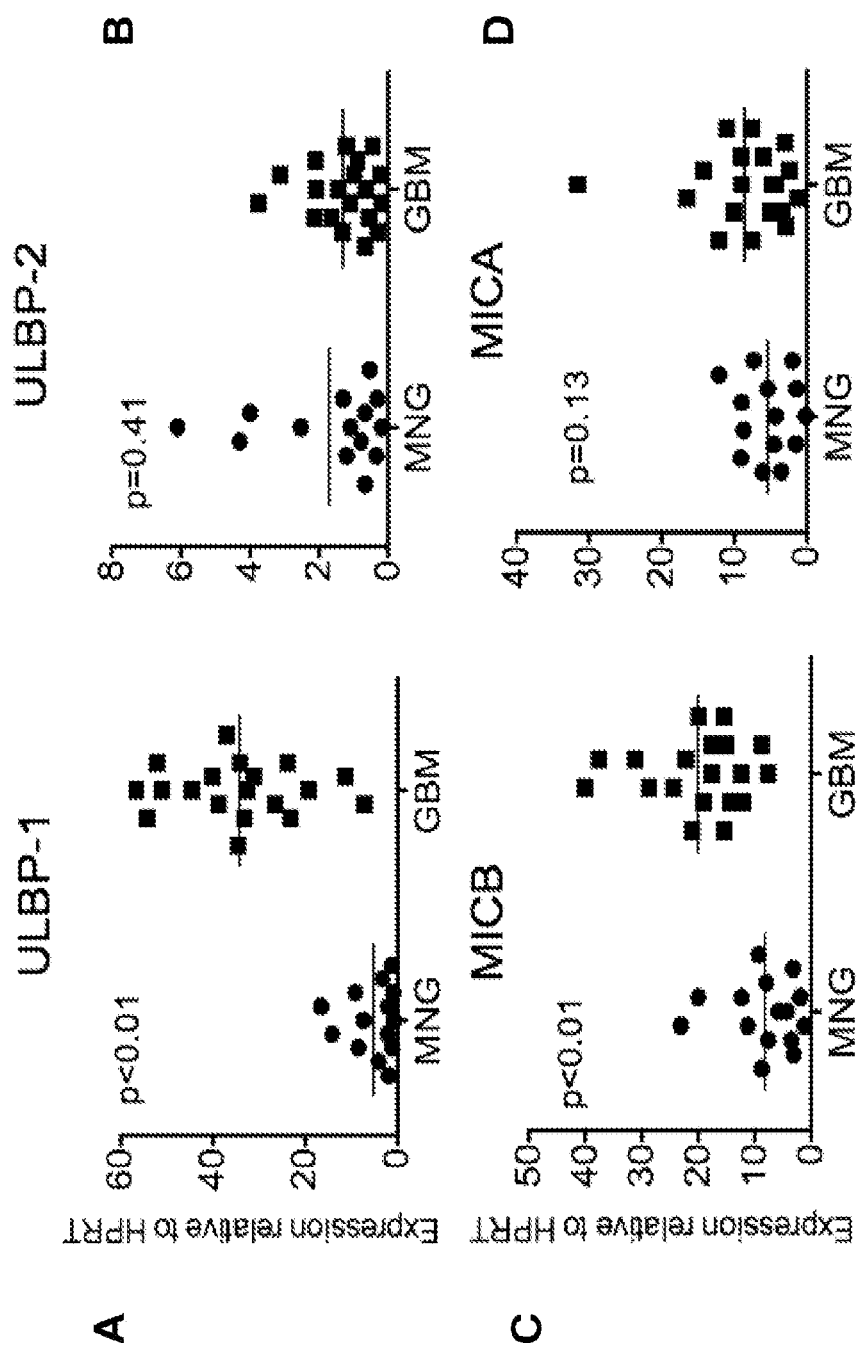
FIG. 5A-D illustrates that mRNA of the NKG2D ligands MICB and ULBP-1 is elevated in GBM patient circulating myeloid cells. Myeloid cells were selected from total PBL. Whole cell mRNA was isolated and reverse transcribed. The resulting cDNA was subjected to quantitative PCR (qPCR) and analyzed relative to the housekeeping gene HPRT.

Myeloid cells express integrins and several classes of adhesion molecules. Tumor cells can secrete or shed NKG2D ligands, which might passively adhere to the surface of myeloid cells. To assess whether circulating myeloid cells express NKG2D ligands at the transcript level, or whether they passively acquire soluble NKG2D ligands secreted by tumor cells, reverse transcription and quantitative PCR was performed using exon-spanning primers. The primers selected for screening span highly conserved exon/exon junctions to account for polymorphisms in the NKG2D ligand genes. Consistent with the flow cytometry data, MICB and ULBP-1 were found to be the most abundantly expressed NKG2D ligands by circulating myeloid cells (FIG. 5) relative to the housekeeping gene HPRT. In patients with GBM (n=19), MICB and ULBP-1 transcript expression was significantly greater than in patients with MNG (n=14, p<0.01). Expression of MICA and ULBP-2, however, were not significantly over expressed in patients with GBM when compared to patients with MNG. By performing whole cell messenger RNA reverse transcription, patient samples were retrospectively tested for expression of other markers, including candidate biomarkers for tumor recurrence or treatment failure.

To confirm that myeloid cell expression of NKG2D ligands was not due to passively acquired soluble NKG2D ligands, an acid wash of PBMC was performed. Acid washing removes passively acquired NKG2D ligands as well as beta-2 microglobulin, a component of the MHC class I complex. Confirming the quantitative PCR data, circulating myeloid cells were found to retain NKG2D ligand expression following an acid wash, but lose beta-2 microglobulin. These data indicate that surface expression detected by flow cytometry is the product of myeloid cell production and surface expression of NKG2D ligands, rather than of passive acquisition of NKG2D ligands secreted or shed by tumor cells.

Figure 6:
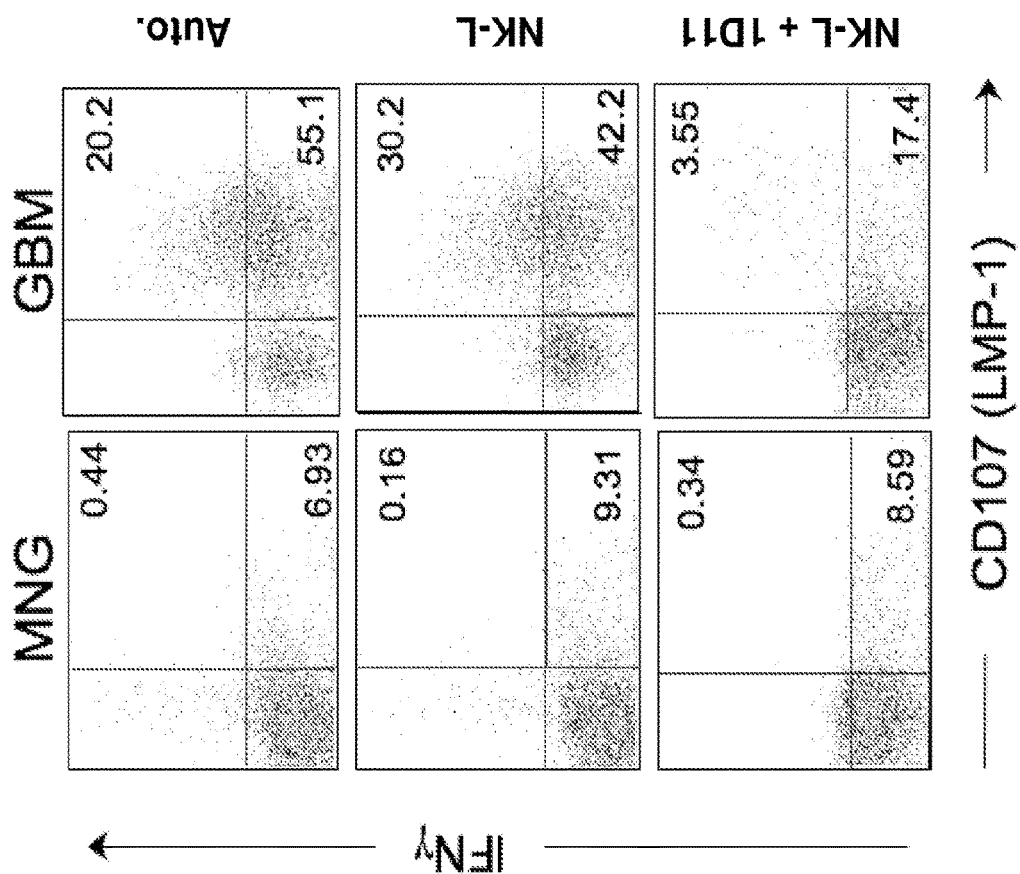
FIG. 6 illustrates that NKG2D ligand-expressing monocytes induce NK cell degranulation and cytokine production in an NKG2D dependent fashion. Circulating myeloid cells were selected from patients with MNG (NKG2D ligand-negative) or GBM (NKG2D ligand-positive) and co-cultured with either autologous (auto) cells or the NKL cell line (in the presence and absence of a neutralizing anti-NKG2D antibody, 1D11) for 3 hours in the presence of PE-conjugated anti-CD107 and brefeldin A. The plots show CD56-gated cells.

Having demonstrated the expression of NKG2D ligands on circulating myeloid cells in GBM patients, whether expression of NKG2D ligands would render these cells sensitive to lysis by NK cells in vitro was assessed. Circulating myeloid cells isolated from GBM patients were found to be targets for autologous IL-2 activated NK cells, inducing degranulation of 55.1% of NK cells and interferon gamma production by 20.2% (FIG. 6). NKG2D ligand-negative myeloid cells isolated from MNG patients, however, induce only background degranulation and cytokine production by NK cells. To ensure that the differences in NK cell populations in GBM and MNG patients did not account for differences in activation, enriched myeloid cells were tested as targets for the NKG2D-positive NK cell line NKL. Myeloid cells from GBM patients induced NKL degranulation and cytokine production, whereas those from MNG patients did not. Addition of 1D11, an NKG2D blocking antibody, significantly decreased (p=0.03) the amount of cytokine production and degranulation of NKL in response to GBM patient-derived myeloid cells, indicating that the activation in vitro is mediated in part by the interaction of NKG2D on NK cells with its ligands on circulating myeloid cells. Together, these data suggest a role for the NKG2D pathway in recognition not only of NKG2D ligand-positive tumor cells, but also for circulating myeloid cells in patients with GBM. However, NKG2D ligand-expressing circulating and tumor-infiltrating myeloid cells are easily recovered from patients with GBM, indicating that a mechanism exists in vivo to prevent NK cell activation and/or lysis of myeloid cells.

Immunotherapy is an evolving and promising modality for treating cancer patients that has not fully made the transition from bench to bedside. Studies using mouse models have determined several successful methods to prevent tumor formation or reduce an established tumor burden in animals. Although this work has resulted in the design and implementation of several clinical trials, there has been limited therapeutic success. Recent work has described the potential for DNA damage caused by radiation and chemotherapy to induce expression of NKG2D ligands on mouse cell lines. To determine if NKG2D ligand expression on myeloid cells in patients with GBM is the result of a stress response to therapy, patient samples were analyzed at the time of initial diagnosis and prior to surgical intervention, steroid treatment, radiation, or chemotherapy. In patients with newly diagnosed GBM (n=10), expression of NKG2D ligands in peripheral blood is readily detectable in myeloid cells, indicating that the expression of NKG2D ligands is the result of tumor burden, rather than DNA damage induced by treatment.

Next whether the induction of NKG2D ligands is dependent on myeloid cell contact with tumor cells, or the result of a soluble factor produced by tumor cells, was assessed. Using a transwell assay, the potential for the U87 GBM tumor cell line to induce expression of NKG2D ligands on peripheral blood mononuclear cells isolated from patients with MNG (NKG2D ligand-negative) was assessed without direct contact between PBMC and U87 cells. Soluble factors secreted by tumor cell lines were found to be sufficient to induce expression of NKG2D ligands on myeloid cells, indicating that direct interaction with tumor cells is not required and that the soluble factor responsible for NKG2D ligand induction on myeloid cells is tumor-derived. As determined during development of the present disclosure, in patients with solid tumors, factors that are secreted by the tumor induce NKG2D ligand expression on myeloid cells. Expression of NKG2D ligands on myeloid cells in circulation and infiltrating tumors impairs NK function, and allows myeloid cells to become targets for activated NK cells. In this way, the tumor continues to recruit a myeloid cell population that can protect tumor cells from elimination by cells of the immune system. Nonetheless knowledge of the mechanism(s) is not needed in order to make and use embodiments of the present disclosure.

Figure 7:
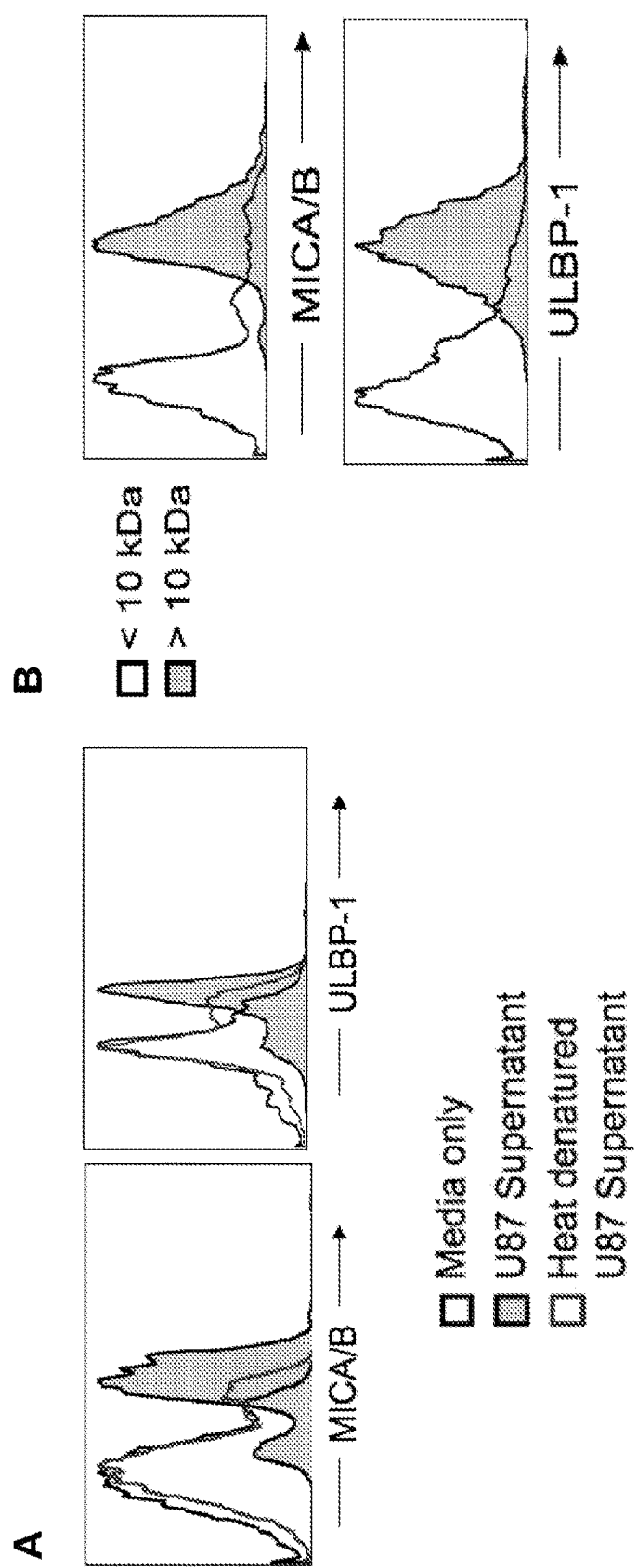
FIG. 7A-B illustrates that heat denaturation but not dialysis of the U87 glioma cell line supernatant reverses NKG2D ligand induction on monocytes. Tumor cell line supernatant was either dialyzed to remove small molecules or concentrated 10x and heat denatured by boiling. About 10% supernatant+90% fresh media was added to myeloid cells isolated from MNG patients for 48 hours and NKG2D ligand expression was analyzed by flow cytometry.

Tumor cells produce an array of soluble factors, including reactive oxygen species and small lipids released into the tumor microenvironment, crossing the blood brain barrier and inducing NKG2D ligand expression by cells in the peripheral blood. To determine whether the responsible soluble factors are large molecules, such as proteins, or small molecules such as lipids or reactive oxygen species, tumor cell line supernatant was dialyzed to remove components smaller than 10 kD and incubated them with NKG2D ligand-negative PBMC isolated from patients with MNG. We find that only soluble factors larger than 10 kD can induce NKG2D ligand expression by myeloid cells (FIG. 7).

Figure 8A:
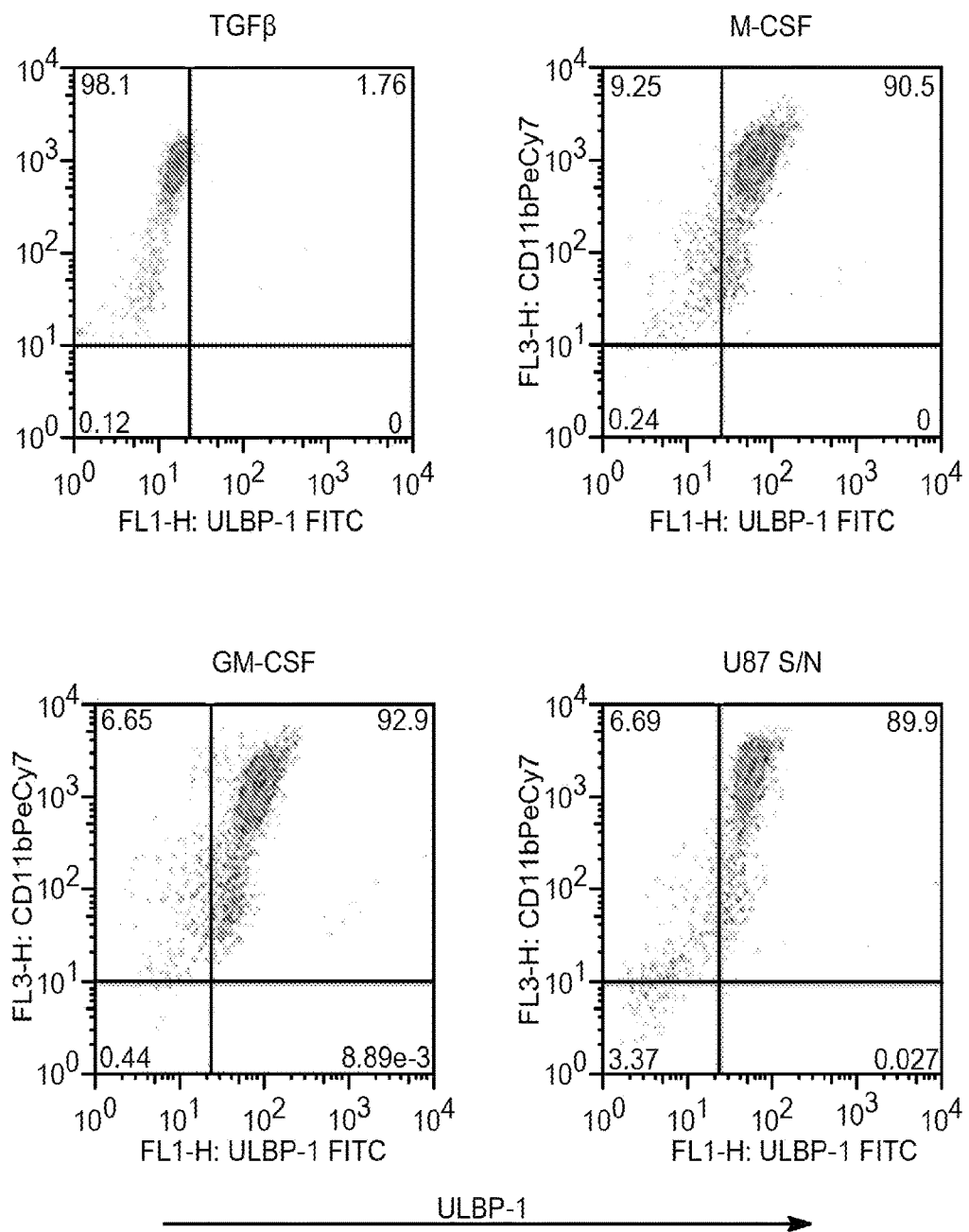
FIG. 8 illustrates that macrophage colony stimulating factor (M-CSF) or granulocyte macrophage colony stimulating factor (GM-CSF) is sufficient to induce monocyte expression of NKG2D ligands. Monocytes from healthy individuals (NKG2D ligand-negative) were incubated with recombinant proteins: VEGF (vascular endothelial growth factor), epidermal growth factor (EGF), IL-2, interferon gamma (IFN-gamma), TGF-beta, M-CSF, GM-CSF and glioma cell supernatant. 48 hours later, monocytes were stained for NKG2D ligands and analyzed by flow cytometry.
Figure 8B:
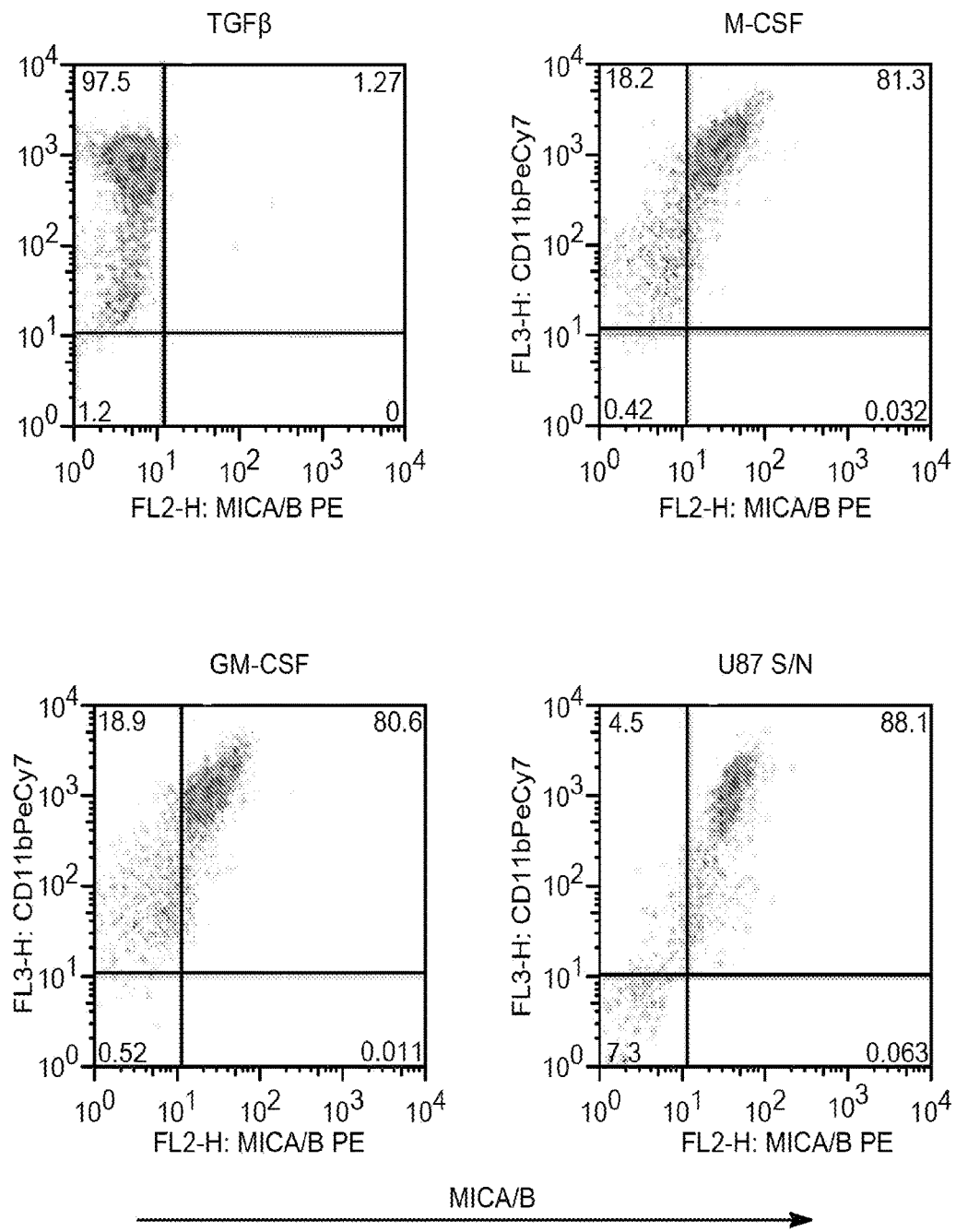
Figure 9:
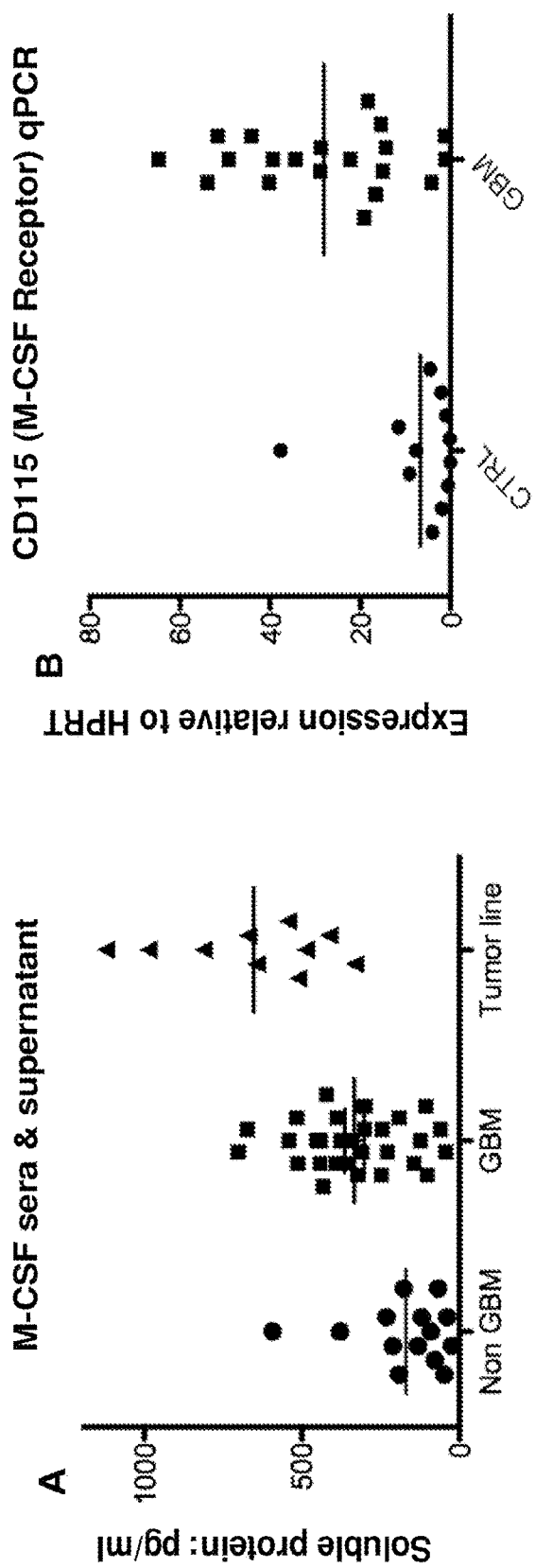
FIG. 9A-B illustrates that M-CSF is detectable in the sera of patients with GBM. Quantities of M-CSF in GBM patient sera and primary patient-derived glioma cell lines were analyzed by ELISA for M-CSF soluble protein expression. Magnetically selected monocytes were analyzed by quantitative PCR for M-CSF receptor expression relative to the housekeeping gene HPRT.

To determine whether the tumor cell-derived soluble factors that induce NKG2D ligands are proteins, tumor cell line supernatants that induce NKG2D ligand expression were concentrated and heat denatured followed by co-culture with PBMC. As shown in FIG. 7, heat denaturation of concentrated tumor cell line supernatant is sufficient to eliminate the increased expression in response to non-denatured tumor cell line supernatant. Based on these data, the factor responsible for NKG2D ligand expression was determined to be a soluble protein produced by the tumor cells. As shown in FIG. 8, U87 supernatant and both M-CSF and GM-CSF, but not TGF-beta, induce expression of NKG2D ligands. Additionally, soluble M-CSF was found in sera from GBM but not non-GBM patients, and in the supernatant of a GBM tumor cell line (FIG. 9).

To determine if soluble NKG2D ligands were responsible for the decreased NKG2D expression that observed in patients with GBM, the sera of GBM patients was compared to non-GBM tumor patients. The sera from GBM patients had greater (n=41, P<0.01) amounts of soluble MICB than patients with MNG (n=30). Fifty-eight percent of the patients examined had soluble MICB present in their sera at levels greater than those observed in MNG patients. In a subset of patients, concentrations of greater than 1 ng/mL were found, whereas a larger subset of patients also contained a group that expressed soluble NKG2D ligands at intermediate levels. Sera from patients with MNG contained low or barely detectable amounts of soluble MICB, suggesting that the shedding and/or secretion of soluble NKG2D ligands may be specific to GBM and not a feature of all patients with a CNS tumor. Patients with soluble MICB in the sera also had detectable soluble MICA, although all sera had less than 1 ng/mL of soluble MICA.

TGF-beta modulates NKG2D expression at the level of transcription. In some cancers, including GBM, where high amounts of TGF-beta can be detected in the sera of patients, it is possible that active TGF-beta can modulate NK and CD8+ T cell activation by actively decreasing mRNA levels of NKG2D. To determine if down-regulation of NKG2D in GBM patients was occurring at the transcript level, NKG2D mRNA in GBM patient NK cells and CD8+ T cells before and after tumor resection was evaluated. In 21 of 24 patients (87.5%), NKG2D mRNA levels significantly increased following tumor resection (P=0.02), indicating that TGF-beta impairs the expression of NKG2D on lymphocytes from GBM patients. To distinguish between soluble ligand and TGF-beta-mediated effects on GBM patient NK and CD8+ T cells, patient sera containing the greatest detected amount of soluble MICB (4.8 ng/mL) was tested to determine whether this amount was sufficient to decrease surface NKG2D expression. Soluble MIC containing sera was able to decrease NKG2D expression. However, NKG2D expression was recovered using a blocking antibody to TGF-beta receptor, indicating that TGF-beta, and not soluble NKG2D ligands, is responsible for decreased NKG2D expression on the GBM patients' lymphocytes. TGF-beta is produced by tumor cells and found in the sera of these patients. However, the source of TGF-beta in the sera of these patients may be either tumor cells or an elevated population of regulatory T cells in GBM patients (Heimberger et al., Clin Cancer Res, 14:5166-5172, 2008). Recent work demonstrates that inhibition of regulatory T cell function, including TGF-beta secretion, can enhance cytotoxic T cell anti-tumor responses (Kong et al., Clin Cancer Res, 14:5759-5768, 2008). As determined during development of the present disclosure, TGF-b-mediated downregulation of NKG2D allows tumor cells in GBM patients to escape recognition by cytolytic effector cells of the immune system, resulting in tumor outgrowth. Accordingly, patients with significant tumor burden may not be ideal candidates for immunotherapy protocols predicated upon T-cell mediated target cell killing.

Figure 10:
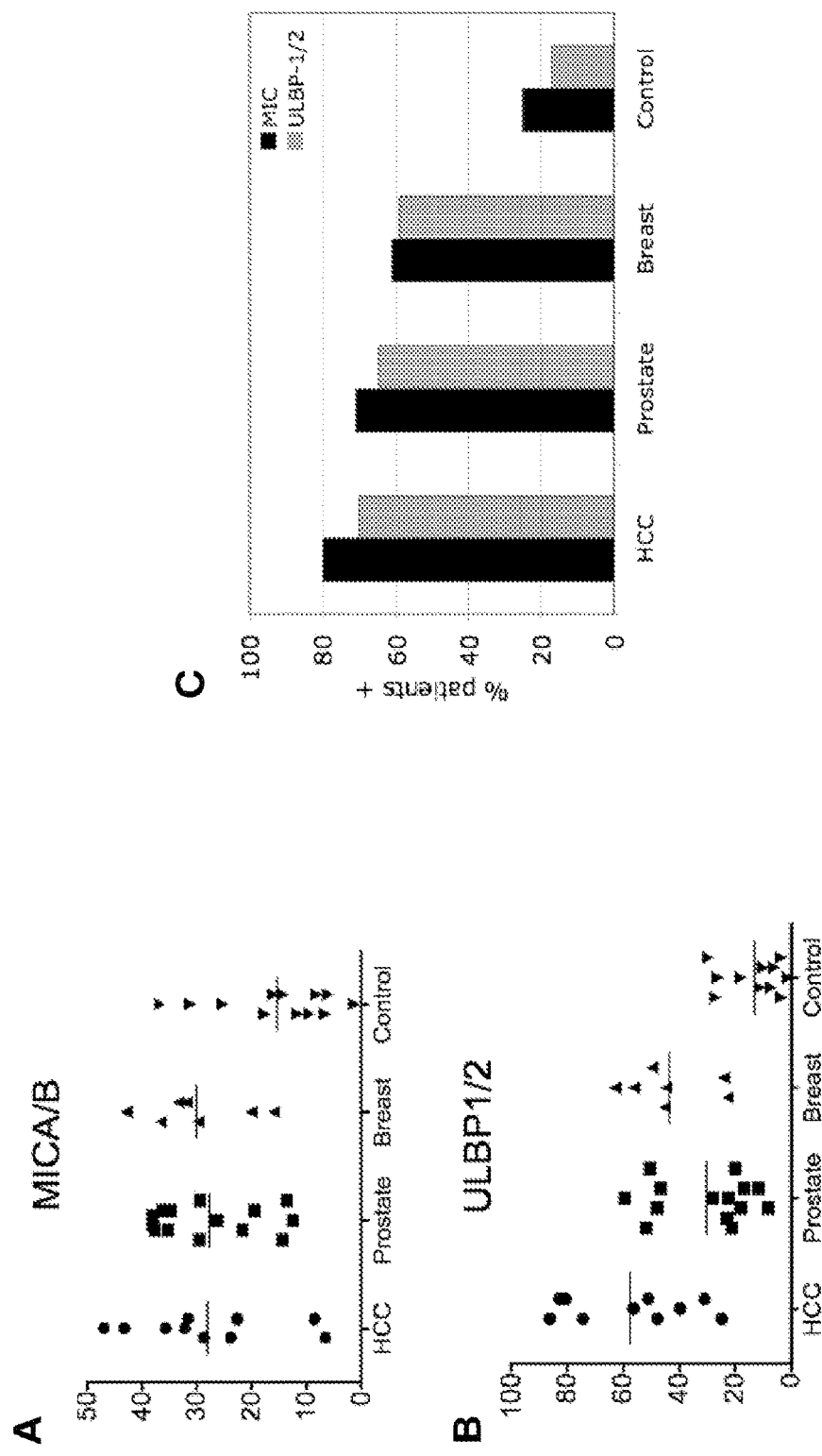
FIG. 10A-C illustrates that patients with a variety of solid tumors express NKG2D ligands on circulating myeloid cells. PBL were isolated from patients with hepatocellular carcinoma (HCC), prostate cancer, breast cancer, and healthy controls without tumors. CD11b+ myeloid cells were analyzed for NKG2D ligand expression by flow cytometry and displayed as a percentage of positive cells relative to cells stained with an isotype-matched control Ig (left and center panels). The percentage of positive patients for NKG2D ligand expression based on mean expression in healthy control subjects.

The presence of NKG2D ligand-bearing myeloid cells in the peripheral blood of GBM patients indicates that NKG2D ligands may be the product of a tumor burden, independent of tumor location. Thus whether NKG2D ligands are expressed in the peripheral blood of patients with other types of solid tumors was assessed. An initial screen included 12 prostate cancer patients, 7 breast cancer patients, and 10 patients with Hepatitis C induced hepatocellular carcinoma (HCC) awaiting liver transplants. NKG2D ligands were detected on circulating myeloid cells in a majority of patients harboring solid tumors as compared to healthy controls (FIG. 10). About 80% of patients with hepatocellular carcinoma (HCC) have significant NKG2D ligand expression on circulating myeloid cells, with a mean of 57.47% of the circulating monocytes expressing ULBP-1, and 27.99% expressing MICA or MICB (p=0.02). The trend is consistent and significant when comparing each type of cancer patient to controls using an unpaired paired t test (p<0.05).

Figure 12:
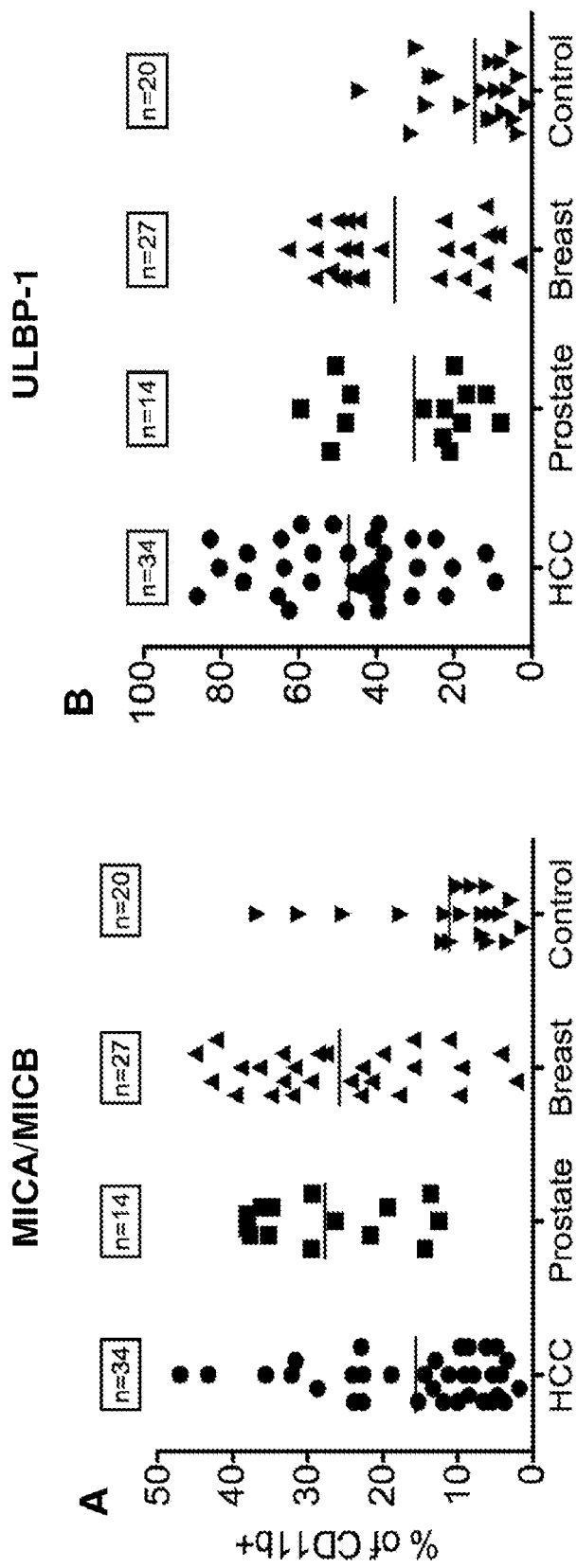
FIG. 12A-B illustrates NKG2D ligand expression on circulating myeloid cells in patients with solid tumors. Freshly isolated peripheral blood mononuclear cells (PBMC) were analyzed by flow cytometry for MICA/B and ULBP-1 expression in 34 patients with hepatocellular carcinoma, 14 patients with prostate carcinoma, 27 patients with breast carcinoma and 20 healthy individuals. After gating on myeloid cells (MHC class II+, CD11b+ cells), samples were analyzed relative to isotype control antibody-stained, donor-matched samples and expressed as % positive over background staining.

An subsequent screen included 14 prostate cancer patients, 27 breast cancer patients, and 34 patients with Hepatitis C induced hepatocellular carcinoma (HCC) awaiting liver transplants. As seen in the initial screen, NKG2D ligands were detected on circulating myeloid cells in a majority of patients harboring solid tumors as compared to healthy controls (FIG. 12). About 50% of patients with prostate cancer have significant NKG2D ligand expression on circulating myeloid cells, with a mean of 28% of circulating myeloid cells expressing MICA or MICB and about 26% of circulating myeloid cells expressing ULBP-1. About 50% of hepatocellular carcinoma (HCC) have significant NKG2D ligand expression on circulating myeloid cells, with a mean of 49.18% of the circulating monocytes expressing ULBP-1, and 17.99% expressing MICA or MICB (p=0.02). A significant number of breast cancer patients (about 70%) express NKG2D ligands on circulating myeloid cells. Within those patients, 26% of myeloid cells express MICA or MICB, and 36% express ULBP-1. The trend is consistent and significant when comparing each type of cancer patient to controls using an unpaired paired t test (p<0.05).

Figure 13:
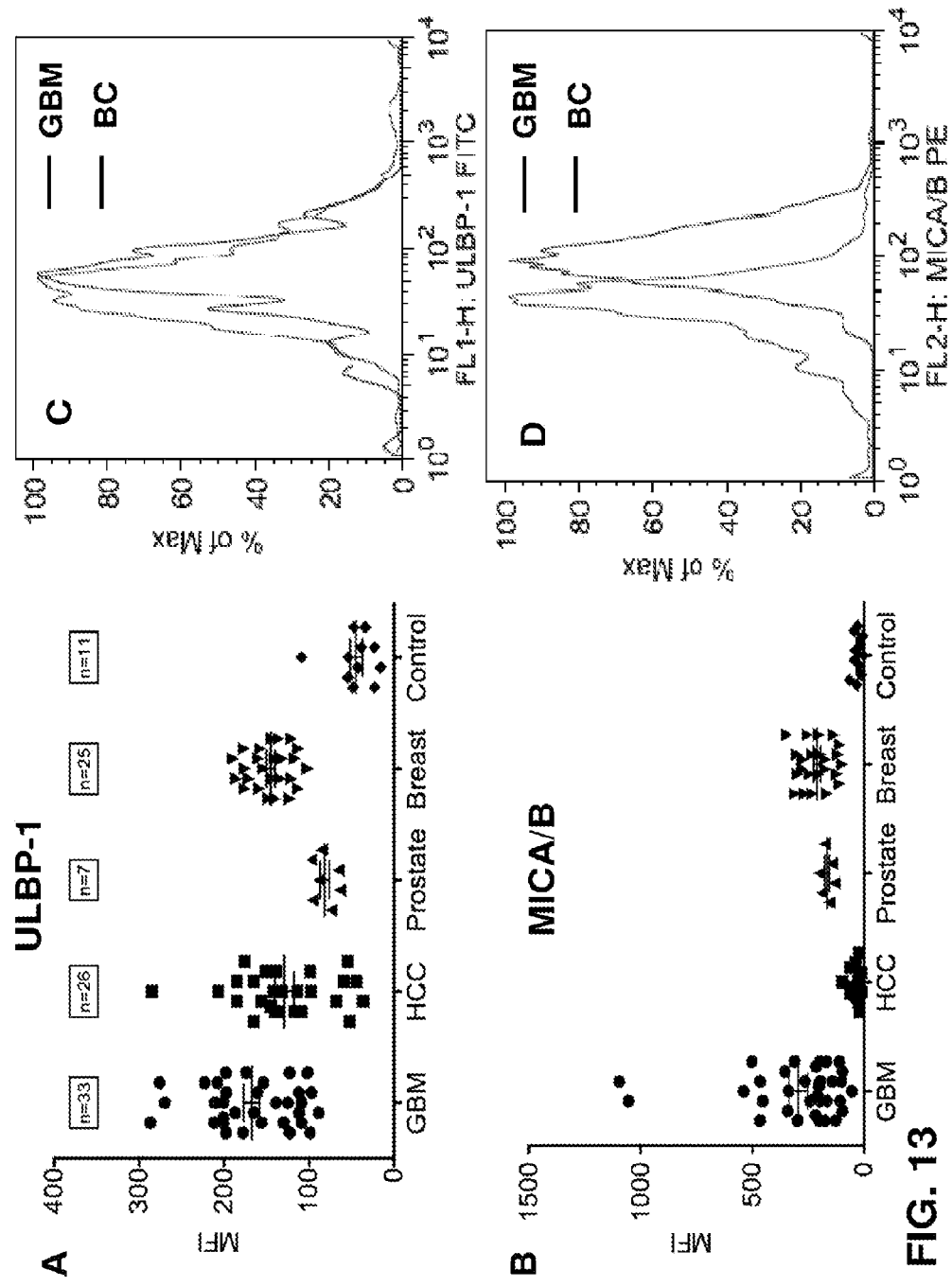
FIG. 13A-D shows the amount of expression of NKG2D ligands on a per cell basis. Freshly isolated PBMC were analyzed for MICA/B and ULBP-1 expression as described in FIG. 12. Positive cells (cells expressing NKG2D ligands over background staining) were then analyzed for mean fluorescence intensity (MFI) as detected by flow cytometry.

In addition to the percentage of myeloid cells that show staining over background, the amount of NKG2D ligands expressed on a per cell basis also indicates varying effects mediated by the tumor. Therefore, the amount of antibody staining, as indicated by Mean Fluorescence Intensity (MFI) was assessed on the positive myeloid cells (FIG. 13). As compared to the robust expression of MICA/B and ULBP-1 as shown in patients with GBM, with MFIs of 297 and 174, respectively, patients with breast cancer have the highest concentration of NKG2D ligands on the surface, with a MICA/B MFI of 190, and a ULBP-1 MFI of 158. Prostate cancer patients express slightly lower amounts, with MFI of MICA/B of 91 and ULBP-1 MFI of 93. HCC patients express relatively low surface amounts of MICA/B, but significantly higher expression of ULBP-1, with a MFI of 118, suggesting that there may be more than one soluble factor secreted by tumors that can induce expression of one or more NKG2D ligands.

Figure 14:
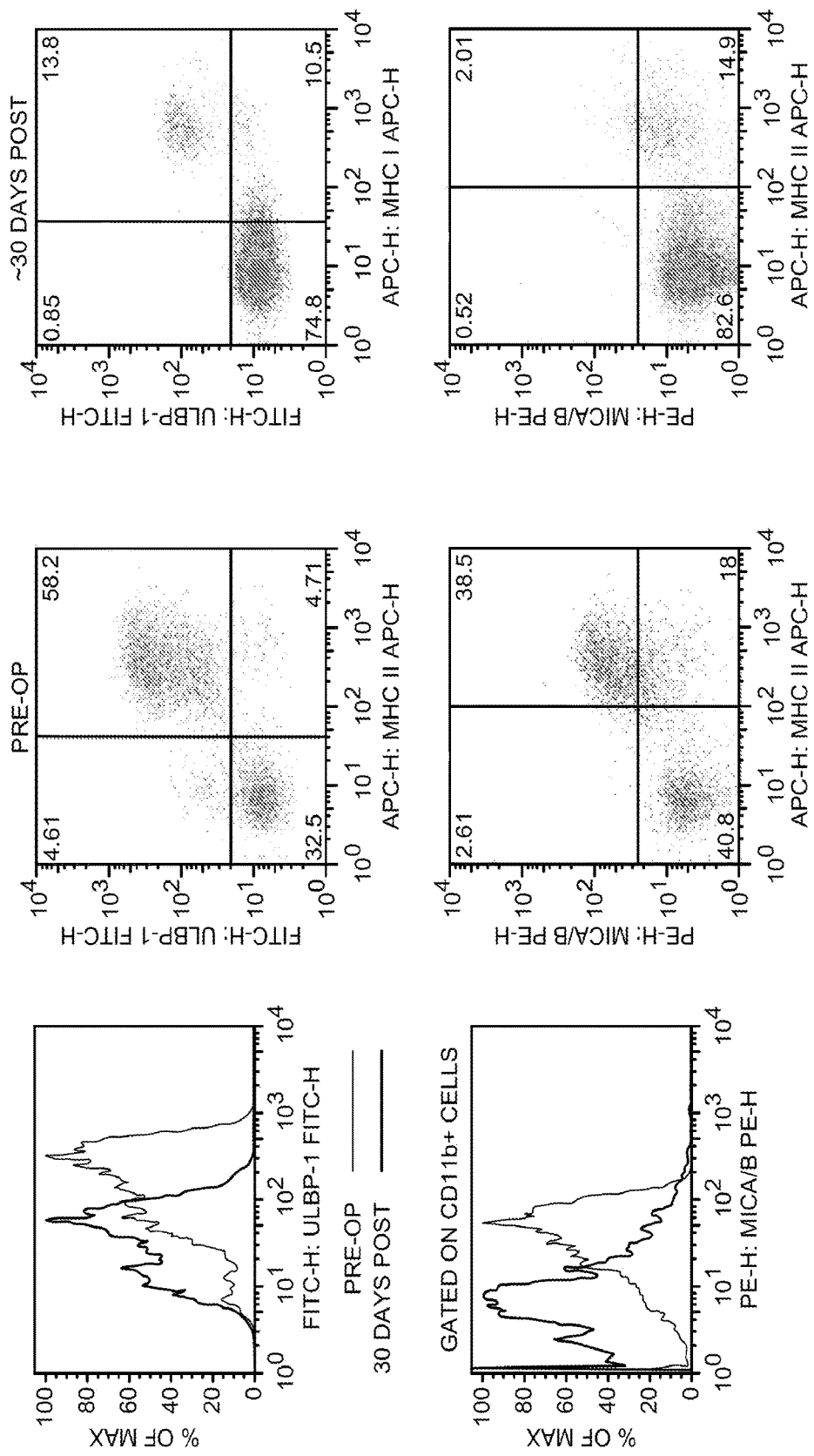
FIG. 14 illustrates that NKG2D ligand expression decreases in patients with GBM following gross total resection of their tumors. Patient PBMC were analyzed by flow cytometry for expression of ULBP-1 (top panels) and MICA/B (bottom panels) prior to tumor resection or approximately 30 days after gross total resection (>90% of tumor mass removed). Plots shown are gated on CD11b+ cells, histograms on left represent the MFI of CD11b+, MHC II+ cells.
Figure 15A:
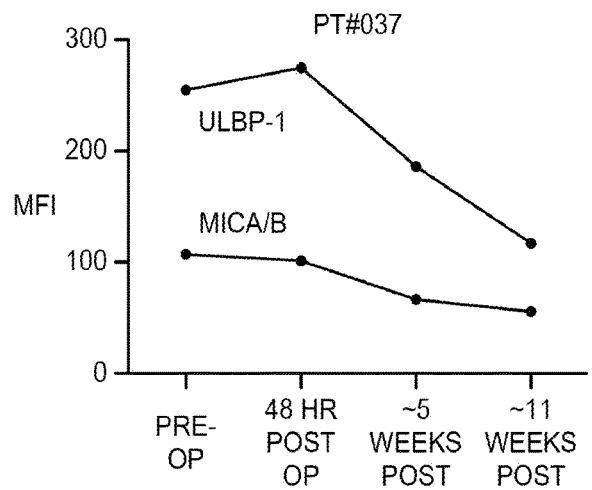
FIG. 15A-F shows that NKG2D ligand expression on circulating myeloid cells decreases over several weeks following tumor resection. Patient PBMC were analyzed for ULBP-1 and MICA/B expression on circulating myeloid cells prior to tumor resection, 48 hours after tumor resection, approximately 5 weeks after tumor resection and approximately 11 weeks after tumor resection. Expression of NKG2D ligands is expressed as MFI of staining on CD11b+, MHC II+ cells.
Figure 15B:
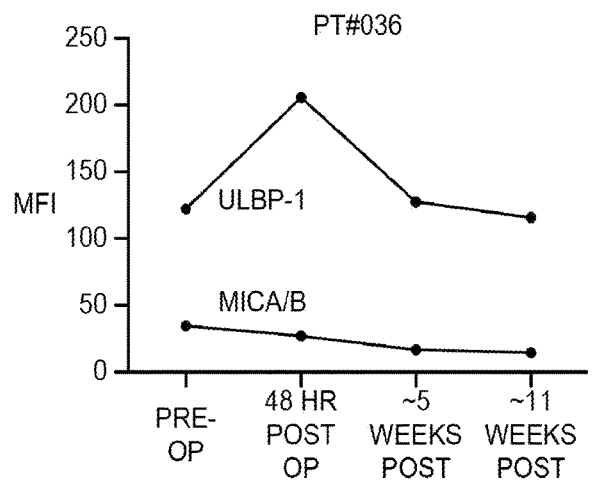
Figure 15C:
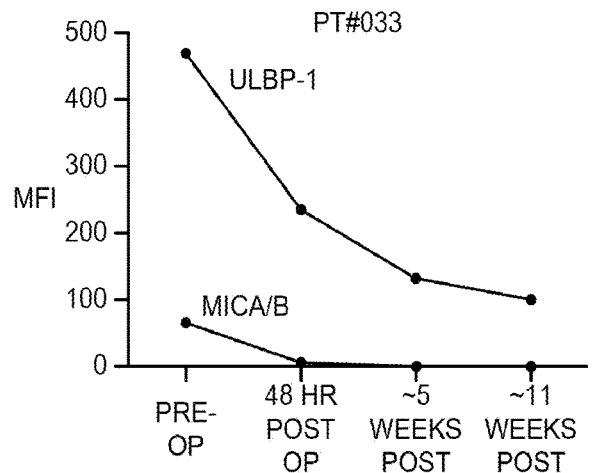
Figure 15D:
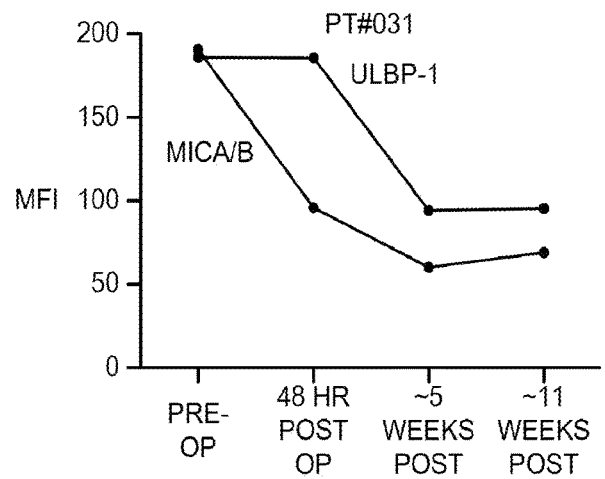
Figure 15E:
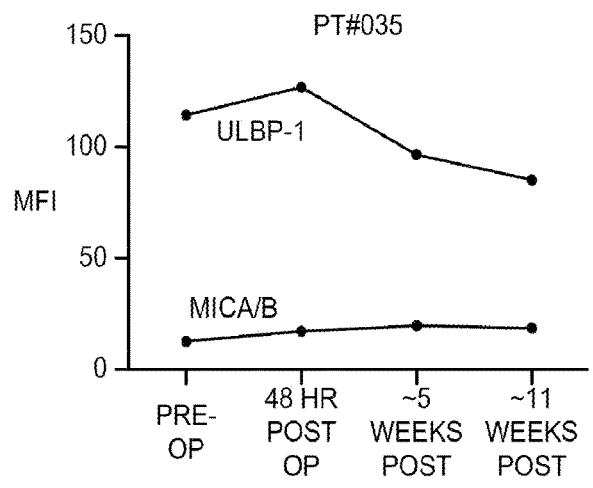
Figure 15F:
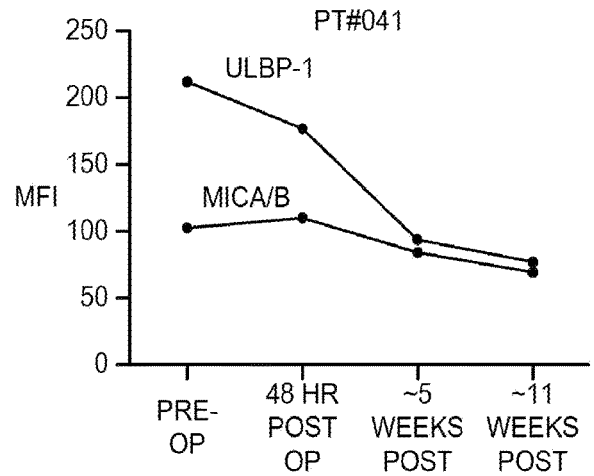
Figure 16A:
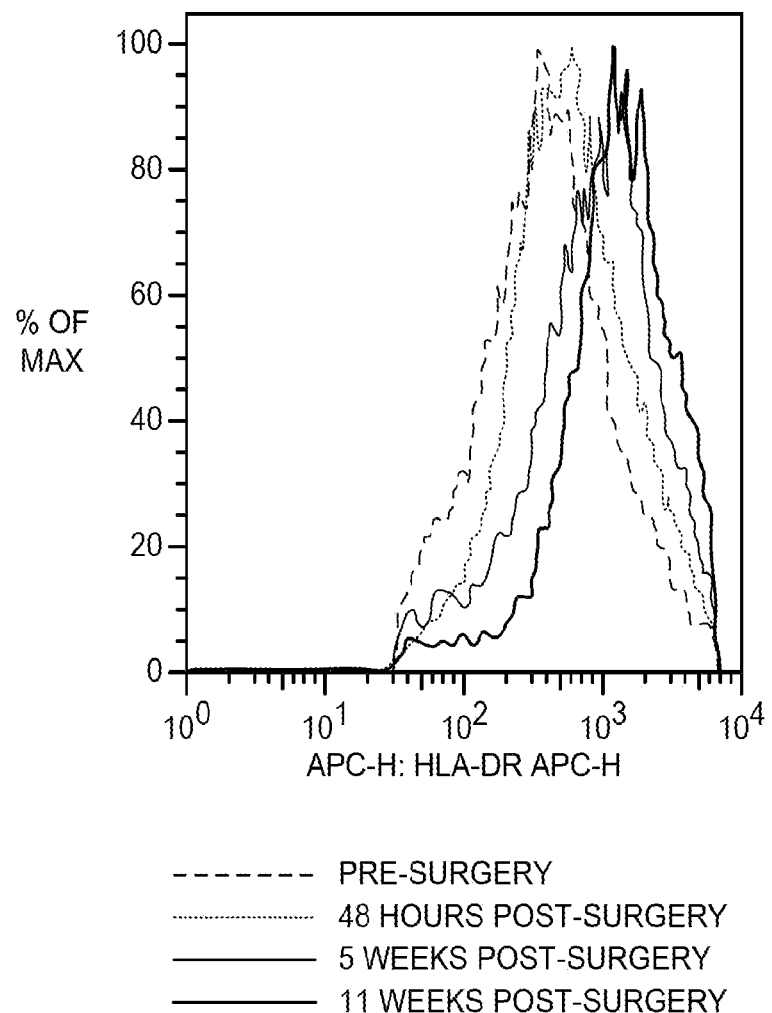
FIG. 16A-D shows that MHC Class II expression increases following tumor resection. Patient PBMC were analyzed for MHC class II expression on circulating myeloid cells prior to tumor resection, 48 hours after tumor resection, approximately 5 weeks after tumor resection, and approximately 11 weeks after tumor resection. Expression of MHC class II is expressed as MFI of staining on CD11b+, MHC II+ cells.
Figure 16B:
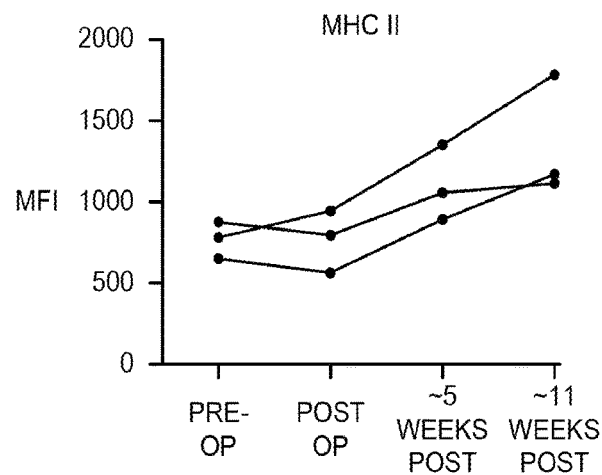
Figure 16C:
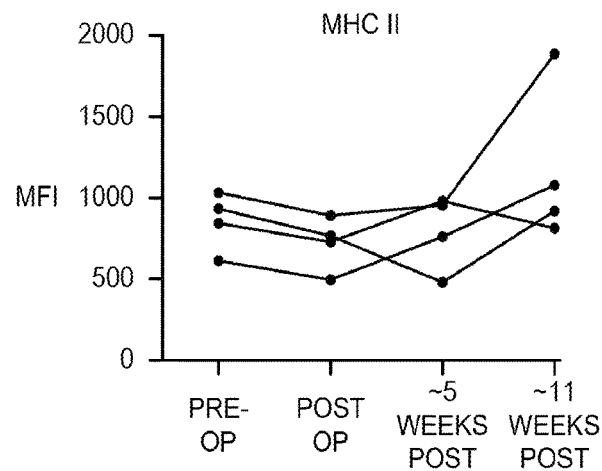
Figure 16D:
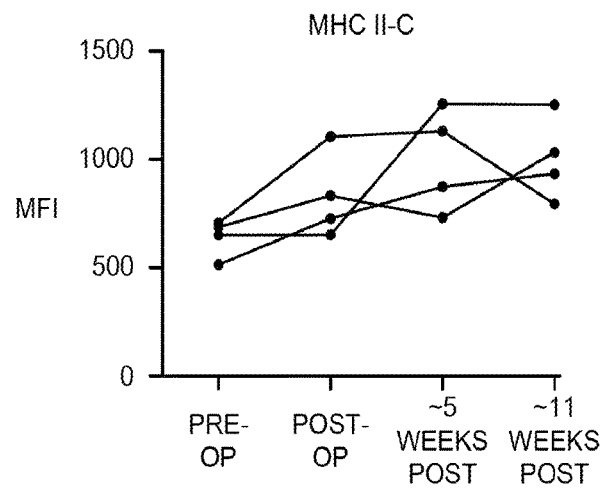

Having shown that NKG2D ligands are expressed in patients with GBM and solid tumors in other locations, the fluctuation in expression following tumor removal was assessed in patients with GBM following a gross total resection (GTR), or removal of >90% of tumor burden. Following GTR, expression of both MICA/B and ULBP-1 are significantly reduced within 30 days of surgery (FIG. 14). To determine whether expression of NKG2D ligands recovers prior to tumor recurrence, myeloid cells from patients without clinical recurrence up toll weeks after surgery as demonstrated by imaging were assayed for expression of NKG2D ligands (FIG. 15). MICA/B expression decreases within 48 hours following surgery, and continues to decline or level off to the levels of expression observed in healthy individuals over the 11-week observation period. Despite a brief increase 48 hours after surgery in some patients, which may be a product of inflammation caused during surgery, ULBP-1 also decreases in patients with a significantly reduced tumor burden over the 11-week observation period.

During assessment of NKG2D ligand expression on circulating myeloid cells, MHC class II (HLA-DR) expression was used to exclude non-myeloid CD11b expressing cells, such as NK cells. Therefore, analysis of MHC II expression was also performed. In contrast to NKG2D ligands, MHC II expression increases following tumor resection, and continues to increase in many GBM patients over the 11-week observation period (FIG. 16). In 2 patients who demonstrated clinical recurrence, MHC II expression began to decline throughout the observation period, suggesting that MHC II expression may serve as an additional biomarker on myeloid cells indicative of solid tumor recurrence.

Various modifications and variations of the present disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments.

We claim:

1. A method for assessing recurrence of and treating glioblastoma multiforme (GBM) in a cancer patient having had GBM, said method comprising:
   a) obtaining a post-treatment blood sample from said patient;
   b) subjecting said post-treatment blood sample from said patient to an antibody based technique for quantitation of expression of a membrane-associated form of at least one NKG2D ligand on myeloid cells of the sample, wherein the at least one NKG2D ligand comprises ULBP1;
   c) diagnosing said patient with recurrence of said GBM when an elevated level of expression of the at least one NKG2D ligand in said post-treatment blood sample is detected as compared to a control blood sample; and
   d) administering one or both of chemotherapy and radiation to said patient diagnosed with recurrence of said GBM.

2. The method of claim 1, wherein the at least one NKG2D ligand further comprises one or both of MICA and MICB.

3. The method of claim 1, wherein the post-treatment blood sample and the control blood sample each comprise peripheral blood lymphocytes isolated by ficoll centrifugation.

4. The method of claim 1, wherein said control blood sample is a blood sample from a tumor free subject, or from said patient at a time when burden of said GBM is known to be minimal.

5. The method of claim 1, wherein said elevated level of expression is detected on CD11b-positive myeloid cells.

6. The method of claim 5, wherein said myeloid cells express one or both of CD45 and MHC class II.

7. A method for assessing prognosis of and treating glioblastoma multiforme (GBM) a cancer patient having GBM, said method comprising:
   a) obtaining a pre-treatment blood sample from said patient; and
   b) subjecting said pre-treatment blood sample from said patient to an antibody based technique for quantitation of expression of a membrane-associated form of at least one NKG2D ligand on myeloid cells of the sample, wherein the at least one NKG2D ligand comprises ULBP1;
   c) determining said patient has a poor prognosis when an elevated level of expression of the at least one NKG2D ligand in said pre-treatment blood sample is detected as compared to a control blood sample from a healthy subject; and
   d) adopting an aggressive treatment regimen for said patient determined to have a poor prognosis, wherein said aggressive treatment regimen involves one or more of surgery, chemotherapy and radiation.

8. The method of claim 7, wherein the at least one NKG2D ligand further comprises one or both of MICA and MICB.

9. The method of claim 7, wherein the pre-treatment blood sample and the control blood sample each comprise peripheral blood lymphocytes isolated by ficoll centrifugation.

10. The method of claim 7, wherein said elevated level of expression is detected on CD11b-positive myeloid cells.

11. The method of claim 7, wherein said myeloid cells express one or both of CD45 and MHC class II.

12. The method of claim 6, wherein the myeloid cells express MHC class II and the MHC class II is HLA-DR.

13. The method of claim 11, wherein the myeloid cells express MHC class II and the MHC class II is HLA-DR.

14. The method of claim 1, wherein the antibody based technique comprises flow cytometry.

15. The method of claim 7, wherein the antibody based technique comprises flow cytometry.

16. method of claim 1, wherein the post-treatment blood sample is obtained from the patient at least one month after resection of the GBM.

17. The method of claim 7, wherein the pre-treatment blood sample is obtained from the patient prior to resection of the GBM.

* * * * *